US011697707B2

(12) United States Patent
Zucchi et al.

(10) Patent No.: US 11,697,707 B2
(45) Date of Patent: Jul. 11, 2023

(54) CHEMICAL SENSORS BASED ON CARBON NANOTUBES FUNCTIONALISED BY CONJUGATED POLYMERS FOR ANALYSIS IN AQUEOUS MEDIUM

(71) Applicants: ECOLE POLYTECHNIQUE, Palaiseau (FR); CENTRE NATIONAL DE LA RECHERCHE SCIENTIFIQUE, Paris (FR); INSTITUT FRANCAIS DES SCIENCES ET TECHNOLOGIES DES TRANSPORTS DE L'AMENAGEMENT ET DES RESEAUX (IFSTTAR), Champs sur Marne (FR)

(72) Inventors: Gaël Zucchi, Gif-sur-Yvette (FR); Bérengère Lebental, Levallois-Perret (FR); Loic Loisel, Arcueil (FR); Sasikumar Ramachandran, Tamil Nadu (IN); Alfredo Flores Gutiérrez, Paris (FR); Xinyang Wang, Palaiseau (FR); Mallesham Godumala, Seoul (KR); Laurence Bodelot, Palaiseau (FR)

(73) Assignees: ECOLE POLYTECHNIQUE, Palaiseau (FR); CENTRE NATIONAL DE LA RECHERCHE SCIENTIFIQUE, Paris (FR); INSTITUT FRANÇAIS DES SCIENCES ET TECHNOLOGIES DES TRANSPORTS DE L'AMENAGEMENT ET DES RESEAUX (IFSTTAR), Champs-sur-Marne (FR)

( * ) Notice: Subject to any disclaimer, the term of this patent is extended or adjusted under 35 U.S.C. 154(b) by 806 days.

(21) Appl. No.: 16/604,423

(22) PCT Filed: Apr. 10, 2018

(86) PCT No.: PCT/FR2018/050903
§ 371 (c)(1),
(2) Date: Oct. 10, 2019

(87) PCT Pub. No.: WO2018/189479
PCT Pub. Date: Oct. 18, 2018

(65) Prior Publication Data
US 2021/0130540 A1 May 6, 2021

(30) Foreign Application Priority Data
Apr. 10, 2017 (FR) ...................................... 1753131

(51) Int. Cl.
*C08G 61/12* (2006.01)
*C01B 32/174* (2017.01)
*G01N 27/12* (2006.01)

(52) U.S. Cl.
CPC .......... *C08G 61/124* (2013.01); *C01B 32/174* (2017.08); *G01N 27/127* (2013.01);
(Continued)

(58) Field of Classification Search
CPC .............. C08G 61/124; C08G 2261/12; C08G 2261/1412; C08G 2261/143;
(Continued)

(56) References Cited

U.S. PATENT DOCUMENTS 7,060,241 B2   6/2006  Glatkowski
7,342,479 B2   3/2008  Glatkowski et al.
(Continued)

FOREIGN PATENT DOCUMENTS

WO    02/076724 A1    10/2002
WO    2005/026694 A2   3/2005
(Continued)

OTHER PUBLICATIONS

Yamamoto et al. (Makromol. Chem. 190, 1649-1654, (1989).*
(Continued)

*Primary Examiner* — Shane Fang
(74) *Attorney, Agent, or Firm* — Nixon & Vanderhye

(57) ABSTRACT

Disclosed are conjugated polymers bearing chemical probes and the use thereof for the preparation of chemical sensors
(Continued)

based on carbon nanotubes allowing the selective detection of analytes in water.

19 Claims, 3 Drawing Sheets

(52) U.S. Cl.
CPC ... *C08G 2261/12* (2013.01); *C08G 2261/143* (2013.01); *C08G 2261/148* (2013.01); *C08G 2261/1412* (2013.01); *C08G 2261/3142* (2013.01); *C08G 2261/3241* (2013.01)

(58) Field of Classification Search
CPC ...... C08G 2261/148; C08G 2261/3142; C08G 2261/3241; C08G 75/32; C08G 75/02; C01B 32/174; G01N 27/127; H01L 51/30; H01L 51/26; H01L 51/558; H01L 51/36

See application file for complete search history.

(56) References Cited

U.S. PATENT DOCUMENTS

| | | | |
|---|---|---|---|
| 9,790,325 | B2 | 10/2017 | Sergent et al. |
| 9,791,597 | B2 | 10/2017 | Zheng |
| 10,106,403 | B2 | 10/2018 | Mayne-L'Hermite et al. |
| 2005/0000830 | A1 | 1/2005 | Glatkowski et al. |
| 2005/0129573 | A1 | 6/2005 | Gabriel et al. |
| 2006/0060825 | A1 | 3/2006 | Glatkowski |
| 2009/0169870 | A1 | 7/2009 | Zheng |

FOREIGN PATENT DOCUMENTS

| | | |
|---|---|---|
| WO | 2005/062031 A1 | 7/2005 |
| WO | 2009/083562 A1 | 7/2009 |
| WO | 2010/034840 A1 | 4/2010 |
| WO | 2014/122406 A2 | 8/2014 |

OTHER PUBLICATIONS

Datta et al., "Controlled functionalization of single-walled carbon nanotubes for enhanced ammonia sensing: a comparative study," J. Phys. D: Appl. Phys. 45 (2012) 355305.

Duvva et al., "Carbazole-based sensitizers for potential application to dye sensitized solar cells," J. Chem. Sci., vol. 127, No. 3, Mar. 2005, pp. 383-394.

Guo et al., "A highly sensitive and rapidly responding fluorescent probe with a large Stokes shift for imaging intracellular hypochlorite," Sensors and Actuators B 236 (2016) pp. 459-465.

Guzow et al., "Photophysical properties of 3-[2-(N-phenylcarbazolyl)-benzoxazol-5-yl]alanine derivatives—experimental and theoretical studies," Photochemical & Photobiological Sciences, 2013, 12, 284-297.

Lin et al., "A Ratiometric Fluorescent Probe for Hypochlorite Based on a Deoximation Reaction," Chem. Eur. J. 2009, 15, 2305-2309.

Liu et al., "Novel chemosensory materials based on polyfluorenes with 2-(2'-pyridyl)-benzimidazole and 5-methyl-3-(pyridin-2-yl)-1,2,4-triazole groups in the side chain," Polymer 48 (2007) 1245-1254.

Miyaura et al., "Palladium-Catalyzed Cross-Coupling Reactions of Organoboron Compounds," Chemical Reviews, 95(7), pp. 2457-2483, 1995.

Wang et al., "Synthesis of Fluorescent Hollow Silica Nanoparticles and Application in Detecting Hypochlorite," Chem. Lett. 2015, 44, 925-927.

Zhang et al., "Electrochemically Functionalized Single-Walled Carbon Nanotube Gas Sensor," Electroanalysis 18, 2006, No. 12, 1153-1158.

Bao et al., "2,2'-Biimidazole-Based Conjugated Polymers as a Novel Fluorescent Sensing Platform for Pyrophosphate Anion," Macromolecules 2012, vol. 45, Apr. 9, 2012, pp. 3394-3401.

Gou et al., "Carbon Nanotube Chemiresistor for Wireless pH Sensing", Scientific Reports, No. 4, Article No. 4468.

International Search Report, dated Jun. 18, 2018, from corresponding PCT application No. PCT/FR2018/050903.

Xing-Hua et al., "Exploiting an Imidazole-Functionalized Polyfluorene Derivative as a Chemosensory Material", Macromolecules, 2004, pp. 7078-7080, vol. 37, No. 19.

Palacios et al., "Hydroxyquinolines with extended fluorophores: arrays for turn-on and ratiometric sensing of cations", Chemical Communications—CHEMCOM, 2007, pp. 3708-3710.

Kan-Yi et al., "Mannose-Substituted Conjugated Polyelectrolyte and Oligomer as an Intelligent Energy Transfer Pair for Label-Free Visual Detection of Concanavalin A", Macromolecules, 2010, pp. 9690-9697, vol. 43, No. 23.

Traina et al., "Design and Synthesis of Monofunctionalized, Water-Soluble Conjugated Polymers for Biosensing and Imaging Applications", Journal of the American Chemical Society, 2011, pp. 12600-12607, vol. 133, No. 32.

Hsu et al., "A carbon nanotube based resettable sensor for measuring free chlorine in drinking water", IEEE Sensors 2014 Proceedings, IEEE, 2014, pp. 1042-1045.

\* cited by examiner

CHEMICAL SENSORS BASED ON CARBON NANOTUBES FUNCTIONALISED BY CONJUGATED POLYMERS FOR ANALYSIS IN AQUEOUS MEDIUM

BACKGROUND OF THE INVENTION

Field of the Invention

The present invention relates to the detection, identification and selective quantification of ionic chemical species in a fluid, typically in aqueous phase. The present invention relates more particularly to a miniature chemical sensor intended particularly for the analysis of aqueous solutions. The sensor comprises carbon nanotubes functionalised on their surface by conjugated polymers bearing suitable chemical groups and enabling such a detection, identification and quantification. The preparation method and the uses of the sensor are described.

Description of the Related Art

In recent years, the demand for reliable methods for detecting chemical species and measuring the concentration thereof has increased considerably, particularly due to the increasing severity of standards in the fields of the environment, food, industrial and household safety or medical diagnostics.

The detection and assay in liquid medium of ionic species is particularly of interest for monitoring water quality, whether to assess the hardness thereof, the degree of disinfection thereof (particularly by tracking chlorine-derived species) or to detect the potential presence of contaminants, for example nitrates, phosphates or cations of heavy metals. Average limit concentrations are already established for these inorganic ions. In this context, the development of high-performance measuring devices is essential.

The detection and precise determination of the concentration of analytes (species to be detected) in liquid, generally aqueous, medium is generally performed by means of laboratory analyses using specialised measurement equipment (particularly FTIR, mass spectrometry, chromatography, atomic absorption, etc.) on samples taken on-site by means of an automatic method or by operators. These techniques make it possible to identify in detail and with great precision all of the analytes present in a sample. However, the need to take samples on-site increases the cost of the analyses drastically and does not allow real-time data collection. Moreover, the instruments used are generally relatively complex, costly and cumbersome systems, rendering them unsuitable for on-site measurements. Furthermore, the response times thereof and/or the time required for the implementation of the measurements are frequently long.

Chemical sensors represent an interesting alternative to burdensome laboratory equipment as they enable on-site detection of ionic species in a fluid, continuously or by means of isolated measurements (over time).

Various criteria are used to qualify chemical sensors, such as the sensitivity or the selectivity.

The sensitivity of a chemical sensor denotes the slope of the curve linking the concentration of the chemical species with the sensor signal variation. The sensitivity is dependent on the target concentration range, which is dependent on the target application. The sensitivity must be the highest possible in the target range. The lowest detectable concentration of the target chemical agent is the limit of sensitivity. It is preferably the lowest possible. In the case of contaminant analysis, it is preferably less than the regulatory limit concentrations. Preferably, the curve linking the concentration and sensor signal is a line. Preferably, the sensitivity is the same when the chemical species concentration increases or decreases. Otherwise, a hysteresis is observed, which must be the lowest possible.

The selectivity of a sensor denotes the ability thereof to detect the target species preferentially to the other species present in solution. This means that the sensitivity of the sensor to the target species largely superior to other species.

Besides these basic constraints, sensor performances may be characterised by other parameters. Thus, it is preferable that the sensor has a small size, that it is simple to manufacture and that it uses small quantities of material so as to have the lowest possible production cost, that it has a low energy consumption during the operation thereof.

The sensor is distinguished from the communicating system which converts the analogue signal from the sensor into digitised data then transmits same to the user. The assembly consisting of the sensor and the communicating system thereof may be referred to as a probe, or measuring node, or also merely as a sensor. Hereinafter, it will be referred to as probe. The probe should transmit the data to the user in the simplest and most user-friendly way possible; also be low-cost, have a low energy consumption, and be as compact as possible.

The sensor may be single-use or function long-term. Long-term, it can provide periodic data (every minute, every hour, once per day, once per month) or continuously. For long-term operation, the service life thereof is an important parameter. The service life is defined as the time during which the response from the sensor (optionally corrected electronically or via software) is correlated with the analyte concentration with the desired precision for the application. The service life may be dependent on the query frequency. Service lives greater than 3 months, preferably greater than or equal to 2 years will usually be sought.

In the case of periodic or continuous use, the response from the sensor may experience drift over time. If this drift is known accurately, it may be corrected electronically or via software. If it is insufficiently known, the sensor should undergo periodic recalibration to ensure the measurement precision sought.

The response time of the sensor (time required to attain 90% of the response after placing in contact with the species to be detected) must be short, as for the recovery time thereof (time required to return to the base value of the signal after evacuating the species in question). The acceptable response times may vary from a few milliseconds to a few minutes according to the application.

Liquid-medium sensors may be classified according to the operating principle thereof. Optical or photometric sensors, which carry out detection by measuring the absorbance and/or light emission of a reactive molecule solution represent a first category. The solution of analytes under test comes into contact with the reagent-probe (in solution or on a substrate). The result is a modification of the properties in respect of absorbance (for example a change of colour) or of light emission of the probe (chemiluminescence, photoluminescence, particularly fluorescence), which makes it possible to retrieve the concentration of the analyte studied. This modification may be observed by the naked eye or measured accurately by optical analysis equipment, that is often somewhat costly, relatively cumbersome and complex to connect to a communicating system. The method is rendered selected by the choice of reagent.

A further category of chemical sensors for the detection of analytes in solution is based on electrochemical or electroanalytical detection methods, i.e. they use electrochemical reactions between a target analyte in solution and (according to the configurations and analytes) two to three electrodes made of finely selected materials and (if necessary) a reference solution (for example mechanically confined around one or a plurality of electrodes by a tube). The materials are chosen according to the target electrochemical reaction. There are a plurality of electrochemical method subcategories, according to the manner in which the electrochemical reaction is converted into electrical data: potentiometric or voltammetric methods. These sensors allow in situ measurements and do not require sampling, but miniaturisation and integration into a communicating system remain complex. This type of sensors operating frequently in solution with respect to a reference electrode, they must be stored under particular conditions when they are not used (as the solution changes over time); they may drift substantially over time and must be recalibrated very regularly (before each daily measurement campaign, generally every week or at best every month).

Voltammetry is a very popular example of these electroanalysis methods. It is based on the measurement of the current flow resulting from the reduction or oxidation of the test compounds present in solution under the effect of a controlled variation of the difference in potential between two specific electrodes. It makes it possible to identify and measure quantitatively a large number of analytes. The choice of the materials of the various electrodes (core and surface coating) makes it possible to adapt the measurement to different analytes. In practice, the voltammetric measurements may be disrupted by the presence of surfactants in the solutions under analysis.

A further category of sensors is based on solid-state electronic devices, the electrical response whereof changes according to the concentration of the analyte sought in the vicinity of the device. The term electronic device denotes herein an electronic component or an assembly of a limited number of electronic components (for example two transistors make up an inverter) to which a voltage, a current or an electromagnetic field may be applied. The response of the device is an electrical quantity (current, voltage, resistance, impedance) or electromagnetic quantity (electric, magnetic field intensity, wave frequency, output power). In this case, the detection principle is based on the change of the physical properties of one or a plurality of the active materials of the electronic device when the latter are exposed to a solution. In particular, some sensors operate by the detection of a variation of resistance (resistive sensors), conductance or impedance of a device, or by the variation of one or a plurality of electrical parameters of a transistor (particularly field-effect), in particular the transconductance, threshold voltage, mobility, leakage current or the saturated or non-saturated state current. Antennas and inverters can also be cited as relevant electronic devices.

The sensitivity to the different analytes and the selectivity are dependent on the different materials chosen for the body of the electric device, which comprises generally a thin layer of metallic or semiconductor, organic or inorganic material, and electrodes.

Sensors based on solid-state electronic devices for fluid analysis are of the most interest, as they are generally simple systems, comprising a layer of sensitive material enabling the recognition of the species with which it interacts, and of a transducer system converting the chemical interaction into an electric signal, which is measured. They have the advantages of not being cumbersome, having a low energy consumption, being inexpensive and offering relatively short response times. They are therefore particularly suitable for on-site measurements and in-line process control. The analysis of the different chemical species generally requires the use of a plurality of sensors sensitive to one or the other of the species or the use of a sensor equipped with manually interchangeable probes.

The field of fluid analysis therefore seeks solutions capable of measuring analytes selectively in real time. Solutions are starting to appear, but they are too cumbersome, too expensive, not sensitive enough or not selective enough, or indeed not rapid enough. They are also difficult to multiplex.

For a number of years, carbon nanotubes have seen a remarkable boom in the field of chemical sensors, where they may be used as a sensitive element forming the basis of the detection system.

Devices based on carbon nanotubes benefit from the large specific surface of these materials, which thus provides a very large interaction surface with the fluid under analysis, and the electrical conductivity thereof is very high. For this reason, carbon nanotubes are found to be extremely sensitive to the adsorption of molecules on the surface thereof, and therefore more generally to the environment thereof. The combination of these properties makes carbon nanotubes a material of great interest as a sensitive element in chemical sensors. Furthermore, the small size thereof is favourable for the production of miniaturised devices.

Numerous types of chemical sensors based on carbon nanotubes are described in the literature, particularly resistive type sensors making use of the system resistance measurement. The layer of sensitive material is sometimes prepared by dispersing the carbon nanotubes in a suitable matrix, which may be inorganic in nature ($SnO_2$, $WO_3$) or polymer in nature, or by functionalising same.

The use of carbon nanotubes functionalised by the conductive polymer poly(1-aminoanthracene) as sensitive elements in sensors has been proposed for pH measurement (A. Star, Scientific Reports 4, Article number: 4468, 2014). Further carbon nanotubes functionalised by organic molecules have been used for measuring free chlorine in drinking water (L. H. H. Hsu et al., Appl. Phys. Lett. 106, 063102, 2015).

Moreover, it is known that the functionalisation of carbon nanotubes in this type of sensor devices makes it possible to increase the selectivity and sensitivity to analytes, in particular in the case of air quality sensors. There has thus been described the functionalisation of carbon nanotubes by poly (N-methyl pyrrole) or polyaniline with a view to enhancing the detection of ammonia (cf. Electroanalysis 2006, 18(12), 1153-1158 or J. Phys. D: Appl. Phys. 45 (2012) 355305), or by a mixture of poly(ethylene imine) and starch for the detection of $CO_2$ (WO 2005/026694, WO 2005/062031).

The application WO 2010/034840 describes a chemical sensor based on functionalised carbon nanotubes, intended to detect gaseous chemical compounds. On the carbon nanotubes are grafted covalently molecules carrying a group G1 (or a precursor of such a group) suitable for reacting with the chemical compound to be detected. The grafted molecules may be cleavable aryl salts or polymers. The measurement of the system resistance is performed using metal electrodes in contact with the film formed by the carbon nanotubes.

U.S. Pat. No. 7,342,479 describes a resistive chemical sensor enabling the detection of analytes in a fluid, wherein the resistive region comprises carbon nanotubes used optionally in combination with a non-conductive polymer that swells or reacts in the presence of the analyte, and optionally organic or non-organic conductors. This polymer then serves as a matrix for the carbon nanotubes and forms non-conductive zones separating the carbon nanotubes, which control conduction.

At the present time, none of the chemical sensors available entirely fulfils the criteria in respect of reliability, rapidity, selectivity, sensitive, portability previously established.

SUMMARY OF THE INVENTION

The aim of the invention is the preparation of a chemical sensor that addresses the needs and the technical problems cited above, i.e. capable of detecting and measuring, in real time, without carrying out sampling by an operator, the presence of ionic chemical compounds in a fluid, rapidly and for a moderate cost.

This sensor needs to be a sensor wherein the sensitivity threshold, which is dependent on the analyte, is low (for example tenth of ppm for hypochlorous acid), selective, readily integrable in electronic devices, non-cumbersome and of the "all-in-one" type, suitable for providing concentrations selectively of a plurality of chemical species present in a fluid.

The present inventors have developed novel families of conjugated polymers, each specially designed for the detection of a specific analyte or of a category of specific analytes. These novel polymers have proven to be capable of functionalising carbon nanotubes in a chemical sensor, both by preserving expected operation of the electronic device, and by promoting electron transfer between the polymer and the carbon nanotubes, thus rendering the sensor sensitive and selective with respect to these analytes.

The aims of the invention are achieved thanks to a conjugated polymer comprising monomer units A chosen from the monomer units of formulas:

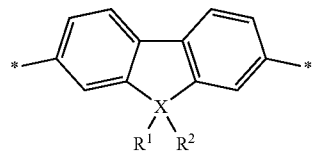

A1

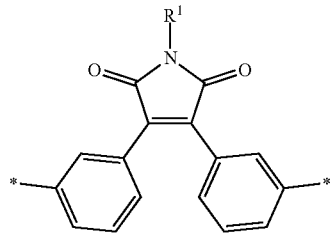

A2a

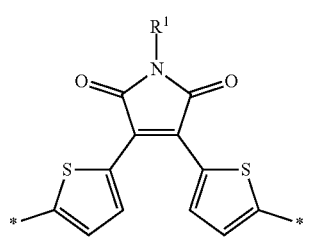

A2b

-continued

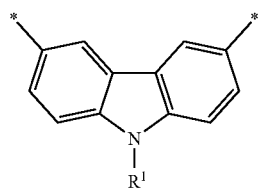

A3a

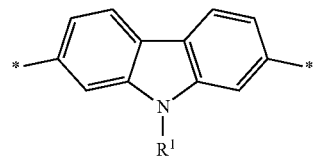

A3b

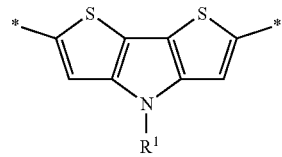

A4

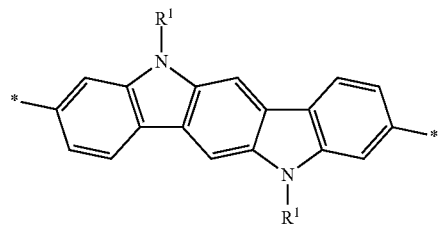

A5

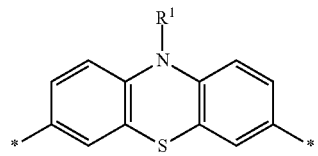

A6

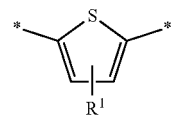

A7

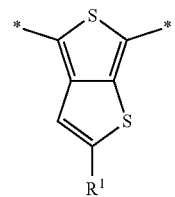

A8

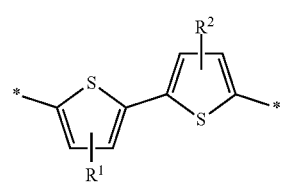

A9

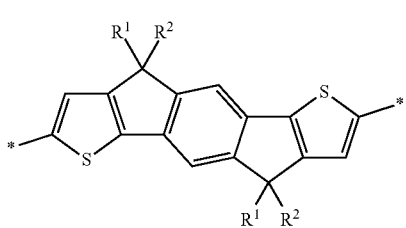
A10 where X denotes a carbon, silicon or germanium atom, $R^1$ and $R^2$, identical or different when they are present in the same monomer unit, are monovalent groups containing at least one group T chosen from the groups oxime, iminodiacetic acid or one of the salts thereof, a polydentate Lewis base including at least two coordinating nitrogen and/or oxygen atoms, a macrocyclic group including from 9 to 36 atoms of which at least 3 heteroatoms chosen from oxygen, nitrogen and the combinations thereof, or a group of formula T1:

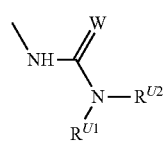
T1 where W denotes a sulphur or oxygen atom, $R^{U1}$ and $R^{U2}$ denote independently a hydrogen atom, an optionally substituted alkyl group or an aryl group, —— denotes the attachment point of the monomer unit to the polymer chain, the carbon atoms of the monomer units A being optionally substituted. An attachment point wherein the origin is situated within a ring indicates that any available carbon atom of the ring may form the attachment point. Similarly, any available carbon atom of the ring may form the attachment point for a group $R^1$ or $R^2$ when the attachment point of these substituents has an origin situated within a ring.

In the case where the group $R^1$ is attached to a nitrogen atom of the monomer unit A, preferably, T denotes neither a group T1 nor an iminodiacetic group or one of the salts thereof.

BRIEF DESCRIPTION OF THE DRAWINGS

The invention will be described in more detail with reference to the appended drawings, wherein.

DESCRIPTION OF THE PREFERRED EMBODIMENTS

Figure 1:
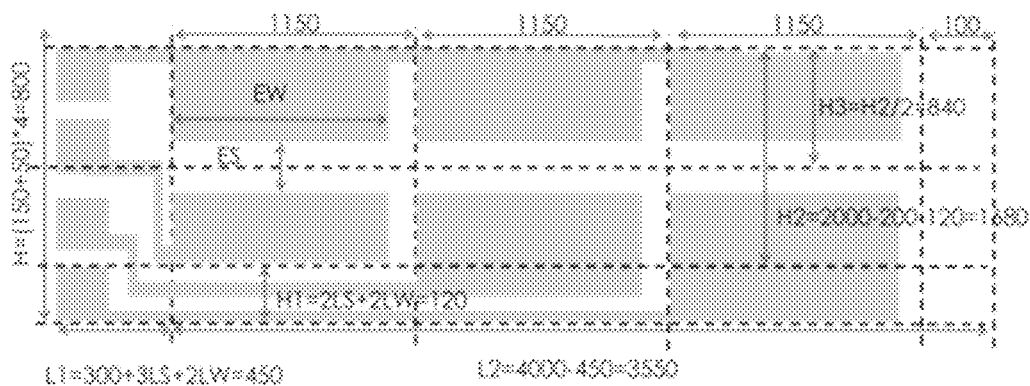
FIG. 1 is an example of design of a chemical sensor according to the invention for three pairs of electrodes.

In the present application, the term "alkyl" denotes a linear or branched, saturated or unsaturated hydrocarbon radial, having from 1 to 25 carbon atoms, including in particular acyclic groups having from 1 to 8 carbon atoms such as methyl, ethyl, n-propyl, isopropyl, butyl, n-hexyl groups, cycloalkyl groups having preferably from 3 to 7 carbon atoms, cycloalkylmethyl groups having preferably from 4 to 8 carbon atoms.

By "substituted alkyl" group is understood an alkyl group as defined above, connected via an $sp^3$ carbon atom and substituted by one or a plurality of aryl groups and/or comprising one or a plurality of heteroatoms such as N, S, O or a halogen atom (fluorine, chlorine, bromine or iodine). Mention will be made by way of examples of arylalkyl groups such as the trityl group (—$CPh_3$), the benzyl group or the 4-methoxybenzyl group, alkoxyalkyl groups, particularly dialkoxymethyl groups such as the diethoxymethyl or dimethoxymethyl groups, the groups $CH_2CO_2R^{11}$, wherein $R^{11}$ represents an optionally substituted or aryl group.

The term "aryl" denotes an aromatic monovalent carbocyclic radical, connected by an $sp^2$ carbon atom, including a single ring (for example a phenyl group) or multiple condensed rings (for example the naphthyl, terphenyl groups), which may optionally be substituted by one or a plurality of groups such as, without limitation, alkyl (for example methyl), hydroxyalkyl, amino-alkyl, hydroxyl, thiol, amino, halogeno (fluoro, bromo, iodo, chloro), nitro, alkylthio, alkoxyl (for example methoxyl), aryloxyl, mono-alkylamino, dialkylamino, acyl, carboxyl, alkoxycarbonyl, aryloxycarbonyl, hydroxysulphonyl, alkoxysulphonyl, aryloxysulphonyl, alkylsulphonyl, alkylsulphinyl, cyano, trifluoromethyl, tetrazolyl, carbamoyl, alkylcarbamoyl, dialkylcarbamoyl groups. Alternatively, two adjacent positions of the aromatic ring may be substituted by a methylenedioxyl or ethylenedioxyl group.

The term aryl also includes "heteroaryl" groups, i.e. aromatic rings wherein one or a plurality of carbon atoms of the aromatic ring(s) are substituted by a heteroatom such as nitrogen, oxygen, phosphorus, sulphur or selenium. The heteroaryl groups may be structures with a single or a plurality of aromatic rings, or structures with a single or a plurality of aromatic rings coupled with one or a plurality of non-aromatic rings. In the structures having a plurality of rings, the rings may be fused, bonded covalently or bonded together via a divalent common group such as a methylene, ethylene, carbonyl group. Examples of heteroaryl groups are the thiophene (2-thienyl, 3-thienyl), pyridine (2-pyridyl, 3-pyridyl, 4-pyridyl), isoxazole, phthalimide, pyrazole, indole, furan groups and the benzofused analogues thereof, phenyl pyridyl ketone, quinoline, phenothiazine, carbazole, benzopyranone.

By monomer unit is understood the group of atoms generated by a single monomer molecule in the structure of a polymer or of an oligomer.

The group T present in the monomer unit A forms the chemical probe of the conjugated polymer according to the invention, and is capable of interacting with an ionic chemical compound to be detected. T is chosen from the groups oxime, iminodiacetic acid or one of the salts thereof, a polydentate Lewis base including at least two coordinating nitrogen and/or oxygen atoms (preferably an aromatic polydentate Lewis base), a macrocyclic group as defined above or a group of formula T1:

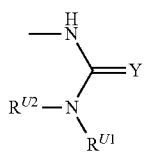

where Y denotes a sulphur or oxygen atom, $R^{U1}$ and $R^{U2}$ denote independently a hydrogen atom, an optionally substituted alkyl group or an aryl group.

It may serve as a coordination site for the targeted ion(s). It may also as a reactive function as in the case of an oxime function, the reaction whereof with hypochlorite ions leads to the formation of an aldehyde function (Sensors and Actuators B 2016, 236, 459-465; Chemistry Letters 2015, 44, 925-927; Chemistry A European Journal 2009, 15, 2305-2309). It may be coupled directly or indirectly to the monomer unit. In the preferred embodiment, the groups $R^1$ and/or $R^2$ are groups of formula -L-T, where L denotes a divalent group, which acts as a spacer group between the chemical probe T and the conjugated chain. The divalent group L is preferentially a group capable of facilitating a movement of electrons between the probe and the chain of the conjugated polymer.

The divalent group L is for example a linear or branched alkylene group, optionally substituted, a cycloalkylene group, optionally substituted, an arylene group, optionally substituted or a combination of the groups cited above of the same category and/or different categories, particularly the cycloalkylenealkylene, biscycloalkylene, biscycloalkylenealkylene, arylenealkylene, bisphenylene and bisphenylenealkylene groups. These groups are considered as substituted alkylene or arylene groups, depending on the case, such as for example the benzylene group which belongs to these two categories. Among the preferred alkylene groups, mention may be made of the C1-C10 linear alkylene groups, for example the methylene group —CH$_2$—, the ethylene group —CH$_2$—CH$_2$—, butylene, hexylene, particularly 1,4-butylene and 1,6-hexylene and the C3-C10 branched alkylene radical such as the 1,4-(4-methylpentylene), 1,6-(2,2,4-trimethylhexylene), 1,5-(5-methylhexylene), 1,6-(6-methylheptylene), 1,5-(2,2,5-trimethylhexylene), 1,7-(3,7-dimethyloctylene), 2,2-(dimethylpropylene) and 1,6-(2,4,4-trimethylhexylene) radicals. Among the preferred cycloalkylene radicals, mention may be made of the cyclopentylene, 4,4'-bicyclohexylenemethylene and cyclohexylene radicals, optionally substituted particularly by alkyl groups.

The group L is preferably an arylene group which ensures superior electron transfer via the bonds, particularly a phenylene, bis-phenylene, tolylene, naphthylene group. Examples of such groups are the 2,4-tolylene, 2,6-tolylene, 2,4-naphthylene, 2,6-naphthylene, 1,5-naphthylene, 1,4-phenylene, 1,4-bisphenylene (-p-C$_6$H$_4$-p-C$_6$H$_4$—), 2-methyl-1,3-phenylene, 4-methyl-1,3-phenylene, tetramethylxylylene groups. The 1,4-phenylene-methylene-1,4-phenylene (4,4-biphenylenemethylene) group is also usable.

The preferred groups T are the oxime, 3-aryl-ureido, 3-aryl-thio-ureido, iminodiacetic acid groups, polydentate Lewis bases included at least two coordinating nitrogen and/or oxygen atoms, and the macrocyclic groups as defined above.

When the group T of the groups $R^1$ or $R^2$ is an oxime group, it represents preferably a ketoxime group of formula —CR═N—OH where R denotes an optionally substituted alkyl or aryl group, or indeed the aldoxime group (—CH═N—OH). The aldoxime group is preferred.

Examples of groups including the oxime function, particularly $R^1$, $R^2$, suitable for use in the invention are represented hereinafter, the attachment point being situated preferably at para of the oxime function, R denoting a hydrogen atom, an optionally substituted alkyl or aryl group, preferably a hydrogen atom:

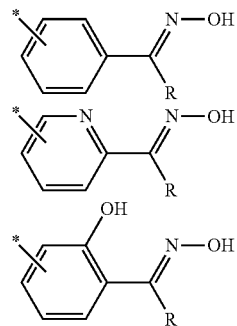

A further category of groups T suitable for use is represented by the groups of formula T1. The preferred groups T1 are those wherein $R^{U2}$=H, i.e. the 3-aryl-ureido, 3-aryl-thio-ureido, 3-alkyl-ureido and 3-alkyl-thio-ureido groups where the alkyl groups present are optionally substituted and preferably C1-C6 groups and the aryl groups are optionally substituted and as defined above. $R^{U1}$ is preferably an optionally substituted alkyl or aryl group, preferably an aryl group, and Y represents preferably an oxygen atom. Of these, the 3-aryl-ureido group (—NH—C(O)—NH—Ar) is preferred. These groups T are preferably connected to the polymer chain via an arylene group such as the 1,4-phenylene group. Examples of groups $R^1$ or $R^2$ corresponding to this embodiment are the (3-aryl-ureido)-aryl, (3-aryl-thio-ureido)-aryl, (3-alkyl-ureido)-aryl, (3-alkyl-thio-ureido)-aryl groups, in particular the 4-(3-phenyl-ureido)-phenyl and 4-(3-phenyl-thio-ureido)-phenyl groups.

In this embodiment, a monomer unit, for example a unit A1, comprises preferably two groups T1, which are preferentially borne by geminate chains, for example by geminate groups $R^1$ and $R^2$.

In a further embodiment, the group T is an iminodiacetic acid group, the formula T2 whereof is recalled hereinafter, and coupled to the remainder of the group $R^1$ or $R^2$ via the nitrogen atom system thereof, or one of the salts thereof:

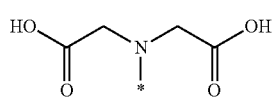

These groups T are preferably connected to the polymer chain via an arylene group such as the 1,4-phenylene group. Examples of groups $R^1$ or $R^2$ corresponding to this embodiment are the groups N-alkylene iminodiacetic or one of the salts thereof, N-arylene iminodiacetic acid or one of the salts thereof.

In this embodiment, a monomer unit, for example a unit A1, comprises preferably two groups T2, which are preferentially borne by geminate chains, for example by geminate groups $R^1$ and $R^2$.

In a fifth preferential embodiment, the group T is a macrocyclic group as defined above and may particularly serve for the detection of $Ca^{2+}$ ions and of metal ions. By macrocyclic group is understood in the present application an organic group comprising at least one heterocyclic structure, which contains carbon, hydrogen atoms, and heteroatoms, chosen particularly from sulphur, nitrogen and oxygen. The macrocyclic group according to the invention includes from 9 to 36 atoms, of which at least 3 heteroatoms chosen from oxygen, nitrogen, sulphur and the combinations thereof, preferably from 4 to 12, and preferably at least 8 carbon atoms.

Examples of such groups are the polyazacycloalkane, polyoxacycloalkane, polythiacycloalkane groups, and combinations thereof, in particular the porphyrin, porphyrazine, chlorine, phthalocyanine, texaphyrin, cyclam and crown ether groups. The size of the macrocyclic group may be easily adapted to the analyte to be detected. Not totally aromatic, preferably non-aromatic, macrocyclic groups are preferred, and of these, aza-, thio- and crown ethers such as 12-crown-4, 15-crown-5, 18-crown-6, dicyclyhexano-18-crown-6, 4-aminobenzyl-15-crown-5, 2-(aminomethyl)-12-crown-4, 2-(aminomethyl)-15-crown-5, 2-(aminomethyl)-18-crown-6, 1-aza-12-crown-4, 1-aza-15-crown-5, 1-aza-18-crown-6, benzo-12-crown-4, benzo-15-crown-5, benzo-18-crown-6, bis[(benzo-15-couronne-5)-15-ylmethyl]pimelate, 4'-bromobenzo-18-crown-6, dibenzo-18-crown-6, dibenzo-24-crown-8, dibenzo-30-crown-10, dicyclohexano-24-crown-8, 4-formylbenzo-15-crown-5, 2-(hydroxymethyl)-12-crown-4, 2-(hydroxymethyl)-15-crown-5, Ia 2-(hydroxymethyl)-18-crown-6, 4-nitrobenzo-15-crown-5, poly[(dibenzo-18-crown-6)-co-formaldehyde]; 12-ane-S3, 14-ane-S4, 1,4,7,10,13-pentaoxa-16-azacyclooctadecane, 1,4,7,13-tetraoxa-10,16-diaza-cyclooctadecane, 1,4,7,10-tetraoxa-13-azacyclopentadecane, 1,4,7,10-tetraoxacyclododecane, 1,4,7,10-tetraazacyclododecane, and 1-aza-4,7-dithiacyclononane.

In a sixth preferential embodiment, the group T is a polydentate Lewis base including at least two coordinating nitrogen and/or oxygen atoms. In one embodiment, it comprises merely coordinating nitrogen atoms. The polydentate Lewis base is preferably bidentate, tridentate or tetradentate, preferentially bidentate, and even more preferentially bidentate with coordinating nitrogen atoms.

Examples of such Lewis bases suitable for use in the groups $R^1$ and/or $R^2$ are, without being limiting, 2,2'-bipyridine (D5, preferential attachment in meta or para position of the nitrogen atom) and the fused derivatives thereof such as 1,10-phenanthroline (D4), 2,9-dimethyl-1,10-phenanthroline, 1,10-phenanthroline-5,6-dione, an imidazo[4,5-f]-1,10-phenanthroline of formula D1, 2,2'-bipyrimidine (D3), 2,2':6',2''-terpyridine (D7), dipyrido-[3,2-a:2',3'-c]phenazine (D2), a 2,6-bis(2-benzimidazolyl)pyridine of formula D6, a 2-(2-pyridyl)benzimidazole of formula D8, thiabendazole (D9), optionally substituted, and where $R^3$, $R^{3a}$ denote independently from one another a hydrogen atom or an optionally substituted alkyl or aryl group, or depending on the case an optionally substituted alkylene or arylene group. All the cyclic carbon atoms of these groups may be substituted, particularly by means of alkyl, aryl, halogen, hydroxyl, carboxyl groups, etc.

Some of these bases are illustrated hereinafter by formulas which are given by way of example (the asterisks next to certain vertices indicate certain preferential attachment points to the remainder of the group $R^1$ or $R^2$). They are generally connected to the remainder of the group $R^1$ or $R^2$ via one of the carbon atoms thereof. In the case of the bases of formulas D1, D6, D8, D9, the connection may also be made via the group $R^3$ or $R^{3a}$, which constitutes the preferential mode of connection. In this case, the group $R^3$ or $R^{3a}$ corresponds to the divalent group L mentioned above and represents generally an arylene group. According to a further embodiment, these Lewis base type groups T are connected directly to the polymer chain, in which case the group T corresponds to the group $R^1$ and/or $R^2$. In a further embodiment, these Lewis base type groups T are connected to the polymer chain via a divalent group L, which may be arylene in nature such as the phenylene, or alkylene group, particularly linear, preferably C3-C10.

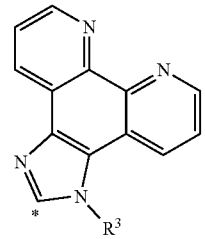

D1

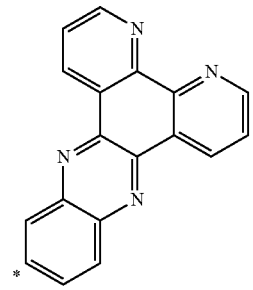

D2

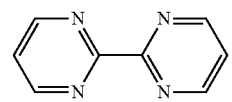

D3

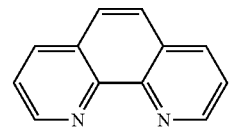

D4

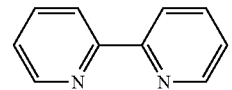

D5

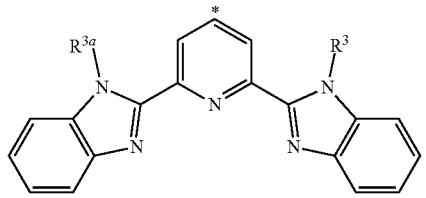

D6

D7

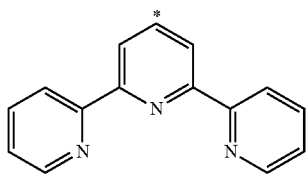

D8

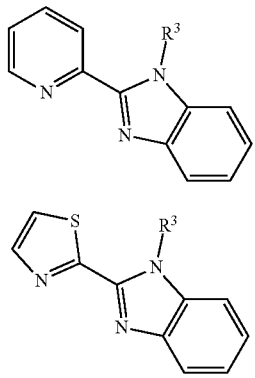

D9

The groups $R^3$ or $R^{3a}$ may particularly be a $C_1$ to $C_6$ alkyl chain terminated by a heterocyclic group, particularly nitrogenous, such as a pyridine group, or a $C_3$ to $C_9$ alkyl chain with a carboxylic acid or carboxylate termination. The 1,10-phenanthroline type Lewis bases are preferably connected via the carbon atom thereof in position 5. The 1,10-phenanthroline, 2,2'-bipyridine and 2,2'-bipyridimidine type Lewis bases are preferably connected directly to the polymer chain ($R^1$ or $R^2$=T).

The monomer units A support a chemical probe capable of interacting with a target analyte. They are preferably chosen from fluorene (A1a, X═C), silafluorene (A1b, X═Si), germafluorene (A1c, X═Ge), 3,4-bis(phenyl)-1H-pyrrole-2,5-dione (A2a), 3,4-di(2-thienyl)-1H-pyrrole-2,5-dione (A2b), carbazole (A3), dithieno[3,2-b:2',3'-d]pyrrole (A4), indolo[3,2-b]carbazole (A5), phenothiazine (A6), thiophene (A7), thieno[3,4-b]thiophene (A8), bithiophene (A9) and 4,7-dihydro-s-indaceno[1,2-b:5,6-b']dithiophene (A10) type units.

In a first embodiment, the monomer unit A is a carbazole unit of formula A3, where L and T are as defined above. Preferably, the group T of the monomer unit A3 comprises at least one oxime function, preferentially, represents the aldoxime function. In a further embodiment, the group T is a polydentate Lewis base including at least two coordinating nitrogen and/or oxygen atoms. More preferably, the group L is a 1,4-phenylene group. The attachment points of the monomer unit A3 to the polymer chain are situated preferably at positions 3 and 6 of the carbazole ring (at the para of the nitrogen atom, A3a), or at positions 2 and 7 of the carbazole ring (at the meta position of the nitrogen atom, A3b):

A3a

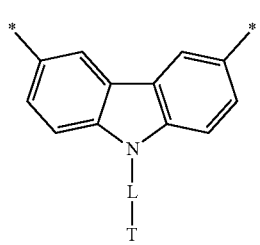

A3b

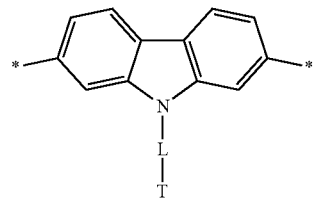

In a second embodiment, the monomer unit A is a fluorene unit of formula A1a, where L and T are as defined above, T being preferentially of formula T1 (monomer unit A1a'), T2 (monomer unit A1a"), or a polydentate Lewis base including at least two coordinating nitrogen and/or oxygen atoms:

A1a

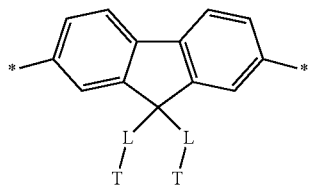

A1a'

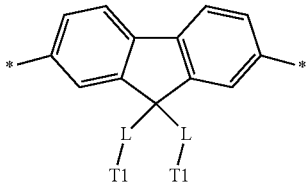

A1a"

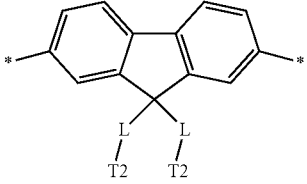

Preferably, the group T1 (urea or thio-urea) of the monomer unit A1a is the 3-phenyl-ureido group. More preferably, the group L is a 1,4-phenylene group. The attachment points of the monomer unit A1a to the polymer chain are situated preferably at positions 2 and 7 of the fluorene ring (at meta of the vertices supporting the $sp^3$ carbon atom).

Preferably, the group T2 (iminodiacetic acid group or one of the salts thereof) of the monomer unit A1a" is an iminodiacetic acid group, connected via the nitrogen atom thereof. More preferably, the group L is a 1,4-phenylene group. The attachment points the monometer unit A1a" to the polymer chain are situated preferably at positions 2 and 7 of the fluorene ring (at meta of the vertices supporting the $sp^3$ carbon atom).

In a preferred embodiment, the conjugated polymer according to the invention comprises monomer units B chosen from the monomer units of formulas:

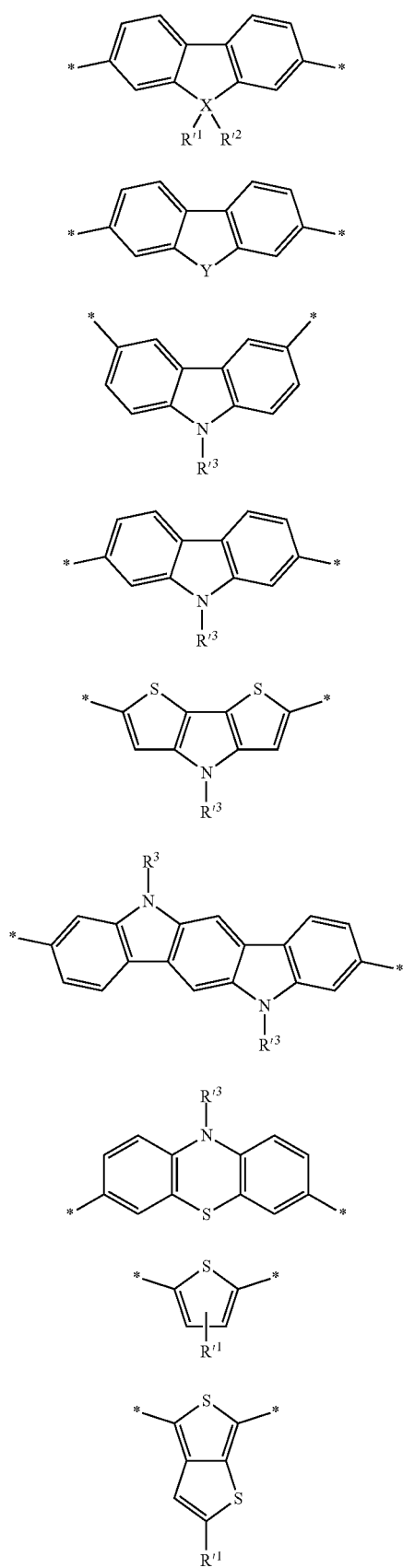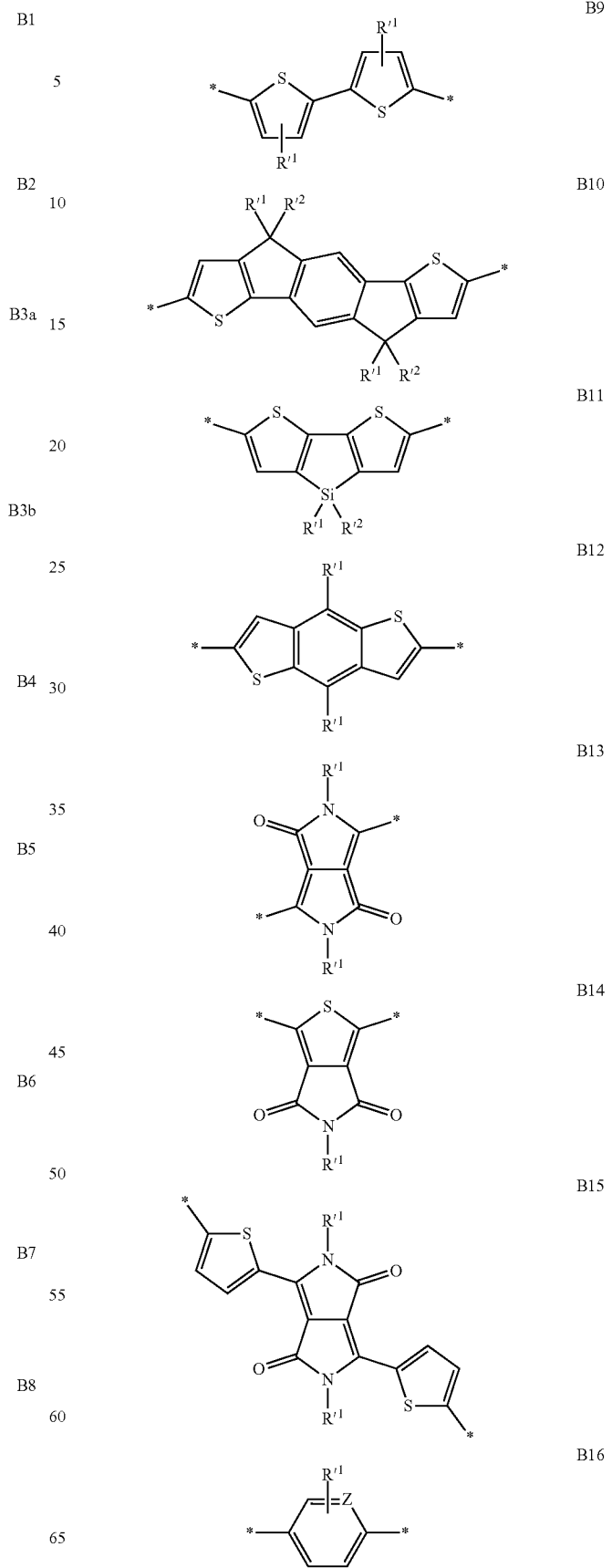

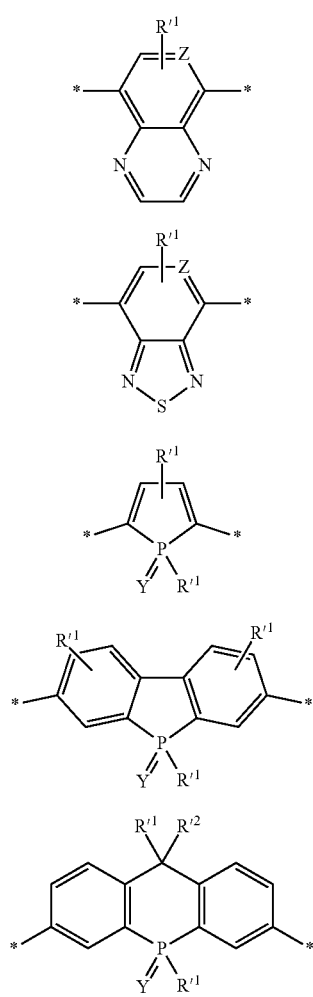

where X denotes a carbon, silicon or germanium atom; Y denotes a sulphur, oxygen or selenium atom; Z denotes a carbon or nitrogen atom, the carbon atoms of the monomer units B being optionally substituted, ——— denotes the attachment point of the monomer unit to the polymer chain, the groups $R'^1$ and $R'^2$, identical or different when they are present in the same monomer unit, preferably identical, represent alkyl or alkoxyl group comprising from 4 to 20 carbon atoms, preferably from 5 to 18, preferentially from 6 to 12 carbon atoms, linear or branched, preferably linear. C6-C8 linear alkyl groups will advantageously be chosen: n-hexyl, n-heptyl, n-octyl, preferably n-hexyl;

the group $R'^3$ represents an alkyl group comprising from 4 to 20 carbon atoms, preferably from 5 to 18, preferentially from 6 to 12 carbon atoms, linear or branched, preferably linear, an aryl group substituted by one or a plurality of alkyl groups comprising from 4 to 20 carbon atoms, preferably from 5 to 18, preferentially from 6 to 12 carbon atoms, linear or branched, preferably linear, or an acyl group of formula —C(O)R$^5$, where $R'^5$ represents an alkyl group comprising from 4 to 20 carbon atoms, preferably from 5 to 18, preferentially from 6 to 12 carbon atoms, linear or branched, preferably linear, the group $R'^4$ represents an aryl group or an alkyl group comprising from 4 to 20 carbon atoms, preferably from 5 to 18, preferentially from 6 to 12 carbon atoms, linear or branched, preferably linear. C6-C8 linear alkyl groups will advantageously be chosen: n-hexyl, n-heptyl, n-octyl, preferably n-hexyl.

The monomer units B are solubilising monomer units supporting side chains, which reduce the formation of polymer aggregates, by limiting in particular the π orbital overlap phenomenon between the conjugated polymer chains, thus avoiding a stack that would result in aggregates that are difficult to solubilise.

The presence of these monomer units may be necessary when a polymer composed essentially or solely of monomer units A encounters dissolution problems in a composition according to the invention intended to functionalise carbon nanotubes. Those skilled in the art will know how to modulate the solubility properties of the conjugated polymer according to the invention by varying the respective quantities of monomer units A and B in this polymer. The conjugated polymer comprises preferentially a molar ratio of monomer units A:B ranging from 100:0 to 1:99 or 10:90, preferably from 50:50 to 10:90.

The preferred monomer units B are the thieno[2',3':4,5]silolo[3,2-b]thiophene (B11), benzo[1,2-b:4,5-b']dithiophene (B12), diketopyrrolopyrrole (B13), thieno[3,4-c]pyrrole-4,6-dione (B14), 2,5-dihydro-3,6-di-2-thienyl-pyrrolo[3,4-c]pyrrole-1,4-dione (B15), phenyl (B16a, Z=C), pyridine (B16b, Z=N), quinoxaline (B17a, Z=C), pyrido[3,4-b]pyrazine (B17b, Z=N), benzothiadiazole (B18a, Z=C), [1,2,5]thiadiazolo-[3,4-c]pyridine (B18b, Z=N), dithieno[3,2-b:2',3'-d]phosphole oxide (B19a, Y=O), dithieno[3,2-b:2',3'-d]phosphole sulphide (B19b, Y=S), dibenzophosphole oxide (Y=O), sulphide (Y=S) or selenide (Y=Se) (respectively B20a, B20b and B20c), phosphaanthracene oxide (Y=O), sulphide (Y=S) or selenide (Y=Se) (X=C, respectively B21a, B21b and B21c), phospha-10-silanthracene oxide (Y=O), sulphide (Y=S) or selenide (Y=Se) (X=Si respectively B21d, B21e and B21f) units.

In a first embodiment, the monomer unit B is a carbazole unit of formula B3a or B3b including an alkyl chain $R'^3$ as defined above.

In a second embodiment, the monomer unit B is a fluorene, silafluorene or germafluorene unit (B1a) including alkyl chains that are optionally identical, preferably identical:

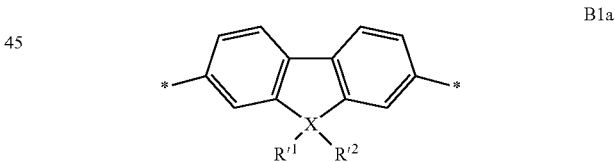

B1a

Generally, the conjugated polymer according to the invention is a copolymer of formula $[(A)_p-(B)_q]_n$, where A and B are the monomer units described above, identical or different, p and q are identical or different integers such that p varies from 1 to 5, preferably from 1 to 2, and q varies from 0 to 20, preferably from 1 to 10, the ratio p:q varying preferentially from 100:0 to 1:99, except for polymers enabling the detection of at least two different analytes that require the presence of at least two probes, in this case the ratio p/q may vary from 99:1 to 1:99 and n denotes the degree of polymerisation (n ranges generally from 3 to 500, preferably from 5 to 250, preferentially from 10 to 200). This formula covers the scenario where a plurality of different monomer units A and/or B are copolymerised statistically. Preferably, p is equal to 1 when q is nil. The ratio p:q may particularly be equal to 1:1, 1:2, 1:3, 1:4, 1:5 or 1:10.

The mean molar mass by number of the conjugated polymer according to the invention varies preferentially from 2,000 to 500,000 g/mol, preferably from 4,000 to 300,000 g/mol, preferentially from 5,000 to 100,000 g/mol.

In a further embodiment, the conjugated polymer according to the invention further comprises monomer units C which include neither group T (chemical probe) as defined above, nor C4-C20 alkyl group, and preferentially chosen from the phenylene, thieno[3,2-b]thiophene, 2,2'-bithiophene, thiophene, selenophene, 2,1,3-benzothiadiazole, 4,9-dihydro-s-indaceno[1,2-b:5,6-b]dithiophene, dithieno[3,2-b:2,3'-d]thiophene and 4,7-bis(thiophene-2-yl)-2,1,3-benzothiadiazole units, optionally substituted.

The respective quantities of the different monomer units A, B and C may be adapted to enhance the solubility of the sensor, modify the interaction thereof with the carbon nanotubes and/or the conduction properties thereof.

The sp$^2$ carbon atoms of the monomer units A, B and/or C according to the invention may be substituted in the same way as the aryl groups as defined in the present application, and the sp$^a$ carbon atoms of the monomer units A, B and/or C according to the invention may be substituted in the same way as the alkyl groups as defined in the present application. These possible substituents are not generally represented on the general diagrams featured in the present description.

The monomer units mentioned above are connected to form a conjugated main chain, either directly to one another, resulting in a biaryl structure, or via double or triple carbon-carbon bonds, in order to preserve a conjugation within the main polymer chain. Biaryl structures are preferred, i.e. advantageously, some or all of the monomers used within the framework of the present invention are monomers suitable for polymerisation by biaryl coupling (see examples 1-4 of the experimental section).

A first conjugated polymer according to the invention more particularly suitable for the detection and quantification of hypochlorite ions is a polymer comprising an oxime type group T, borne by monomer units A chosen from carbazole (A3), dithieno[3,2-b:2',3'-d]pyrrole (A4), indolo[3,2-b]carbazole (A5), phenothiazine (A6) units, preferably from carbazole units of formula A3. These further comprise preferentially monomer units B including preferably the fluorene structural unit, functionalised by C6-C20 alkyl groups, preferentially identical. In a further embodiment, this conjugated polymer may further comprise monomer units C (not supporting chemical probes T or C4-C20 alkyl groups) of phenylene, thieno[3,2-b]thiophene, 2,2'-bithiophene, thiophene or dithieno[3,2-b:2,3'-d]thiophene type, optionally substituted.

More preferably, in this embodiment, the first conjugated polymer has the following formula:

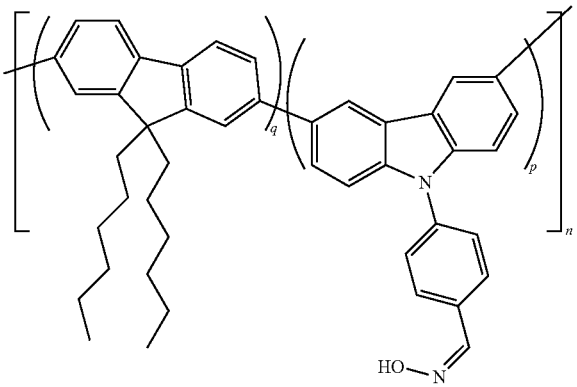

wherein p, q and n are as defined above. The polymer including two n-octyl groups instead of n-hexyl groups in the formula above is also preferred.

A second conjugated polymer according to the invention more particularly suitable for the detection and quantification of anions such as chlorides, nitrates or phosphates and of the mixtures thereof is a polymer comprising a group T of formula T1 (urea or thio-urea), supported by the monomer units A1 wherein the groups $R^1$ and $R^2$ are preferentially identical. These polymers further comprise preferentially fluorene type monomer units B, where $R^4$ and $R^5$ are C6-C20 alkyl groups, preferentially identical, and optionally monomer units C not supporting chemical probes T or C4-C20 alkyl groups, of phenylene, thieno[3,2-b]thiophene, 2,2'-bithiophene, thiophene or dithieno[3,2-b:2',3'-d]thiophene type, optionally substituted.

More preferably, in this embodiment, the second conjugated polymer has the following formula:

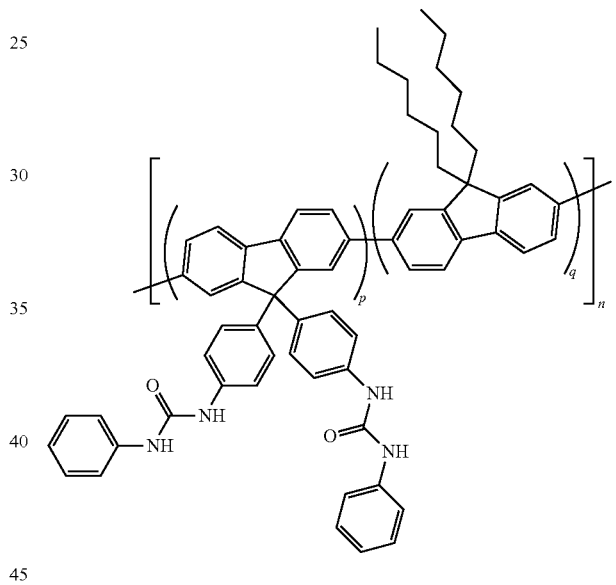

wherein p, q and n are as defined above. The polymer including two n-octyl groups instead of n-hexyl groups in the formula above is also preferred.

A third conjugated polymer according to the invention more particularly suitable for the detection and quantification of $Ca^{2+}$ and $Mg^{2+}$ ions (water hardness measurement) is a polymer comprising a group T of formula T2 (group T including an iminodiacetic acid group or one of the salts thereof), supported by the fluorene type monomer units A (A1a), wherein the groups $R^1$ and $R^2$ are preferentially identical. These polymers further comprise preferentially fluorene type monomer units B where $R'^1$ and $R'^2$ are C6-C18 alkyl groups, preferentially identical, and optionally monomer units C not supporting chemical probes T or C4-C20 alkyl groups, of phenylene, thieno[3,2-b]thiophene, 2,2'-bithiophene, thiophene or dithieno[3,2-b.2,3'-d]thiophene type, optionally substituted.

More preferably, in this embodiment, the third conjugated polymer has the following formula:

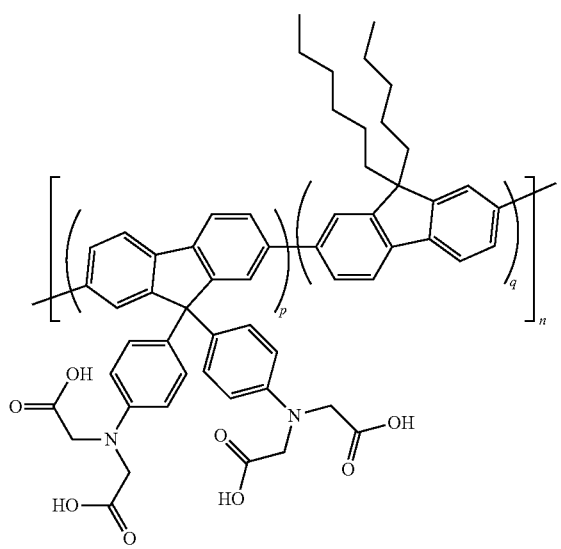

wherein p, q and n are as defined above. The polymer including two n-octyl groups instead of n-hexyl groups in the formula above is also preferred.

A fourth conjugated polymer according to the invention more particularly suitable for the detection and quantification of heavy metal ions is a polymer comprising a polydentate Lewis base type group T including at least two coordinating nitrogen and/or oxygen atoms, supported by monomer units A chosen from carbazole, dithieno[3,2-b:2', 3'-d]pyrrole, indolo[3,2-b]carbazole and phenothiazine units. These polymers further comprise preferentially monomer units B as defined for the third conjugated polymer according to the invention. In a further embodiment, this conjugated polymer may further comprise monomer units C, as defined above.

More preferably, in this embodiment, the fourth conjugated polymer has the following formula:

wherein p, q and n are as defined above. The polymer including two n-octyl groups instead of n-hexyl groups in the formula above is also preferred.

The chemical reactions used for the preparation of the conjugated polymers according to the invention are well-known to those skilled in the art, and use polycondensation catalysed by palladium, copper or nickel complexes. Polymers having a biaryl structure may be obtained by Suzuki-Miyaura coupling (cf. N. Miyaura, A. Suzuki, Chem. Rev., 1995, 95, 2457-2483), which involves reacting an aryl or vinyl halide (or a pseudo-halide such as a triflate) with an arylboronic or vinylboronic acid or ester, catalysed by palladium. Heck, Stille, Negishi, Kumada, Sonogashira or Ullmann type cross-couplings may also be used to form biaryl, stilbenic (connection of monomer units via an alkene function), diarylacetylenic (connection of monomer units via an alkyne function using a Sonogashira coupling) or diarylamine type (connection of monomer units via an amine group using an Ullmann coupling) structures.

A great advantage of the conjugated polymers according to the invention lies in that they can be synthesised from readily accessible monomers, particularly from commercial derivatives, in particular in the case of fluorene type monomer units (A1a) wherein $R^1=R^2=$n-hexyl, n-octyl or 2-ethylhexyl.

Typically, precursor monomers of the monomer units A and B are used for the synthesis of the polymers according to the invention, each supporting two halogenated, preferably brominated, aromatic reactive groups, and/or arylboronic acid or ester in the case of a Suzuki-Miyaura coupling. In this scenario, one of the monomer generally supports at least two halogenated aromatic reactive groups and at least one further monomer generally supports at least two arylboronic acid or ester reactive groups.

Optionally, there may be performed after the polymerisation reaction a chain-end reactive group suppression reaction ("end-capping") by reacting with a suitable chemical compound, so as to prevent any risk of reaction of the conjugated polymer with compounds present in the medium under analysis. Thus, as is well-known to those skilled in the art, an aryl halide end group could be converted into a non-reactive biaryl group by Suzuki-Miyaura type coupling

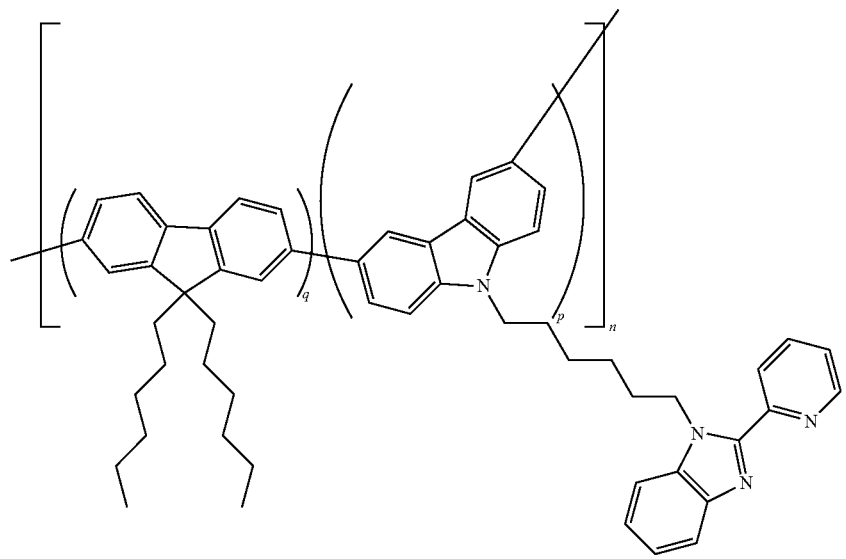

with an arylboronic acid such as phenylboronic acid or the pinacol ester thereof, and an arylboronic acid or ester end group could be converted into a non-reactive biaryl group by Suzuki-Miyaura type coupling with an aryl halide such as bromobenzene.

The preparation of the various precursor monomers makes use of conventional organic chemistry reactions, particularly arylations of carbazoles or phenothiazines by aryl halides catalysed by copper (Ullmann coupling), alkylations of amines by methyl bromoacetate for the preparation of iminodiacetic acid derivatives, condensation of amines with isocyanates or isothiocyanates for the preparation of ureas or thio-ureas, condensation of carbonylated compounds with hydroxylamine for the preparation of oximes, brominations, aryl halide coupling reactions with tetrahydroxydiboron ($[B(OH_2)]_2$) for the preparation of arylboronic acids, etc.

The chemical probe T of the conjugated polymer is preferably present in at least one of the precursor monomers of the conjugated polymer according to the invention. Alternatively, at least one of the monomers may support a precursor group of the chemical probe, which will be converted into said probe after the polymerisation reaction.

By "precursor group of the chemical probe" is understood, within the scope of the present invention, a group which, by the nature thereof, cannot interact directly with the targeted analyte, but which may, by a simple chemical reaction, result in a group suitable for such an interaction. Such a precursor may, for example, be a group protected by a protective group or group which will result in the chemical probe following a substitution reaction well-known to those skilled in the art. Example 1 of the present application thus involves the preparation of a conjugated polymer comprising monomer units having benzaldehyde functions, which are converted during a final step into the chemical probe per se (benzaldoxime group) by reacting with hydroxylamine.

Preferably, the carbon nanotubes present in a sensor are functionalised by a conjugated polymer supporting a single type of chemical probe, in order to carry out selective detection.

The present invention therefore relates to novel conjugated polymers intended to detect and/or assay at least one chemical compound when they are associated with carbon nanotubes.

The carbon nanotubes used within the scope of the present invention may be chosen within all known categories of carbon nanotubes. The carbon nanotubes are generally presented in the form of single or multiple cylindrical layers of graphene. The individual layers may vary in terms of arrangement and functionality. They may particularly consist of multi-walled nanotubes, also known as MWNT, such as double-walled nanotubes, or indeed single-walled nanotubes, also known as SWNT. They may undergo various purification, sorting (by diameter, by chirality or by semiconductor or metallic nature) or activation treatments such as annealing, acidification (which may facilitate a covalent functionalisation) or sonication before being functionalised by the polymers described according to the invention. These treatments are particularly intended to increase the performances thereof, such as the sensitivity thereof.

The carbon nanotubes preferably have an outer diameter ranging from 0.5 nm to 150 nm, preferentially from 1 to 100 nm and more preferentially from 1 to 10 nm. The length thereof may vary from 50 nm to 1 mm, preferably from 500 nm to 50 µm. They may behave like metallic or semiconductor materials, depending on the tube diameter, the orientation of the hexagonal carbon atom lattices with respect to the tube axis, or the number of walls.

These carbon nanotubes are functionalised by at least one semiconductor polymer according to the invention. The conjugated polymer according to the invention is a semiconductor organic polymer wherein the main chain is 7-conjugated and essentially formed of aromatic groups.

The conjugated polymer according to the invention comprises at least one monomer unit including a chemical group suitable for interacting with at least one ionic species. Such a chemical group is generally grafted onto a side chain of the conjugated polymer and shall be referred to as chemical probe in the present application.

The conjugated polymers according to the invention have been designed, by means of the selection of suitable monomers, to have, on one hand, an affinity with the carbon nanotubes and to be able to interact therewith, and, on the other, to exhibit an affinity with a targeted analyte. These conjugated polymers thus have side chains which support specific chemical probes of the ions under analysis, capable of chelating/complexing the ions in solution or of reacting therewith. Weak bonds of the Van der Waals force type, electrostatic interactions, hydrogen bonds, appear between the chemical probe and the analyte, which reversibly forms a complex therewith. These side chains also act as a spacer. In the case of a chemical reaction between the probe and the targeted analyte, this is reversible, which is ensured by the existence of a reaction suitable for regenerating the initial probe function. The regeneration is performed for example by steeping the sensor in a basic hydroxylamine chloride solution.

The analytes interact with the conjugated polymer probes, creating an electronic and/or geometric disturbance transmitted to the carbon nanotube via the conjugated chain itself having received the data via the side chains or directly through space. There results a modification of the resistance of the carbon nanotube, enabling the detection and assay of the analyte.

The interaction between the carbon nanotubes and the conductive polymers may be of non-covalent or covalent nature. In the case of a covalent interaction, the surface of the carbon nanotubes is modified by grafting the conductive polymer, and this polymer therefore comprises a function involved in the covalent bond with the surface of the carbon nanotube. It will be preferred to use non-covalent type functionalisation (for example "π-stacking" type between the nanotubes and the conjugated polymer chains), so as to minimise the impact on the conduction properties of the carbon nanotubes.

The sensitive material of the ionic species sensor according to the invention is composed of two main elements: an ionic recognition system, which helps ensure the selectivity of the sensor and is provided by the side chains supporting probes of the conjugated polymers (which can act as ligands with respect to the analytes when there is no chemical reaction between the analyte and the probe), and a signal transduction system, provided by the carbon nanotubes and the main chains of the conjugated polymers.

The present inventors have developed sensors configured to respond selectively in the presence of specific ionic analytes, the selectivity whereof results from the specific chemical functionalisation undergone by the conjugated polymers equipping the carbon nanotubes. In an embodiment, the sensor is configured to detect selectively at least two analytes and comprises in the structure thereof at least two different monomer units A enabling the detection of different ionic compounds via the presence of at least two different chemical probes T.

An example of a polymer suitable for selectively detecting hypochlorite ions and heavy metal ions comprises the two following categories of monomer units, the molar ratio thereof being capable of varying from 99:1 to 1:99:

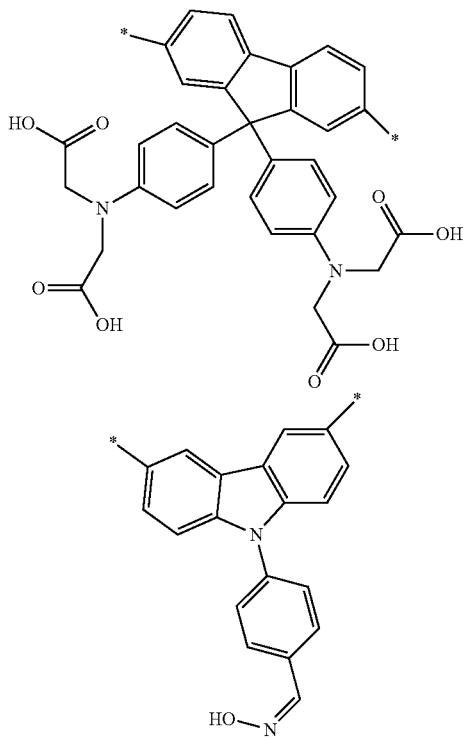

The chemical sensor according to the present invention, intended for the detection and/or assay of one or a plurality of ionic chemical species in a fluid, comprises a flexible or rigid support, and at least two electrodes disposed on said support, the support being at least partially coated with a composition layer comprising carbon nanotubes functionalised by at least one conjugated polymer according to the invention, said composition layer ensuring electrical contact between the electrodes and forming the sensitive element of the sensor.

The sensor according to the invention can function according to various electronic transduction modes, i.e. the functionalised carbon nanotubes can be used as an active material in various forms of electronic devices, particularly resistor, transistor, antenna, resistor, inverter. It comprises generally 2 or 4 electrodes when it consists of an ohmic device (according to whether the resistance or the resistivity is measured), and generally 3 or 4 electrodes when it consists of a transistor.

In the preferred embodiment of the invention, the chemical sensor is an ohmic sensor, i.e. a resistive sensor, which uses particularly the relatively low resistance of the carbon nanotubes as a means of transduction for the detection of a given chemical compound. The resistance of the functionalised carbon nanotubes which provide the contact between the two electrodes is measured between these electrodes. Under the effect of the analyte interacting with the conjugated polymer, the resistance of the carbon nanotubes varies in a specific manner which is dependent on the type and the concentration of the species detected.

The support comprised in the sensor according to the present invention may be a support of any type and shape suitable for implementing the present invention. It generally consists of a support having a planar or substantially planar surface. It must be made of an insulating material such as, without limitation, silicon, silica, glass, silicon nitride, a polymer, particularly ETFE, Kapton, fibreglass, PEI. The surface area of the support is dependent on the size of the electronic device and on the number of devices produced on the same support. It may vary from 0.1 mm² to several m², preferably from 0.5 mm² to 0.1 m² (A3 format).

The electrodes comprised in the device according to the present invention are typically situated on either end of the sensitive zone of the sensor, i.e. at opposite ends of this zone. They are formed from a conductive material. Said electrodes comprise preferably at least one metal or alloy type metallic material or conductive metal oxide, advantageously chosen from Au, Pd, Pt, Al, Cr, Ni, Ti, ITO (tin-doped indium oxide), W and steel, a multilayer material or a metal/metallic material composite material such as Ti/Au, Cr/Au, Ti/Pd or Ti/Au, or indeed a nanomaterial composite such as carbon nanotubes, graphene, reduced graphene oxide. The electrode material will be particularly chosen for the lack of electrolysis reactions in water in the voltage range used to operate the sensor.

The (conductive) electrodes may also be of any shape suitable for implementing the present invention, for example two rectangular and parallel electrodes. Advantageously, the electrodes used in the device according to the invention exhibit an interdigital comb, spiral or concentric configuration, preferably, interdigital comb comprising, for each electrode, generally at least 3 arms.

In a further embodiment, one or both electrodes exhibit a peak effect with respect to the other electrode (for example the electrodes are facing each other by one of the right angles thereof). This makes it possible to concentrate the electrical field lines to increase the sensitivity.

In the case of an antenna sensor, the electrode forming the antenna may exhibit any acceptable antenna configurations according to the operating frequency range in question.

Any technique known to those skilled in the art suitable for preparing on the surface of a support at least two separate electrodes is suitable for use within the scope of the present invention. The electrodes are preferentially formed by printing or by vacuum deposition particular by vaporisation, spraying, or plasma-assisted vapour phase deposition. The geometry and relative positioning of the electrodes will be determined by those skilled in the art according to the type of sensor sought and the size of the carbon nanotubes used. In the case of two parallel rectangular electrodes, the spacing between electrodes varies preferentially from 100 to 10000 μm. The length of the side whereby the electrodes face each other varies preferentially from 400 to 10000 μm. FIG. 1 gives an example of design for three pairs of electrodes, where LS denotes the spacing between the electrical connection tracks between the contact pads and the electrodes (30 μm), LW denotes the width of said connection tracks (30 μm), EW denotes the width of the electrodes, ES the spacing between the electrodes. The lateral dimension of the contact pads is 300 μm and the spacing thereof 200 μm.

The contact pads serve particularly to connect the sensor to electronics for reading and communication to the user, via the creation of welds or microwelds. The welding may take place directly on the electrodes, in which case the pads are not required. The scanning and communication electronics may be positioned on the same substrate (in this case the pads are not required) or on a different support. The pads, when they are required, may be positioned on the front face of the sensor (same face as the sensor) or on the rear face (for example to protect same from exposure to liquid). Those skilled in the art will define the suitable connection strategy according to the application constraints (particularly sensor size, conditions of use).

Any deposition method suitable for locating and distributing the functionalised carbon nanotubes sufficiently homogeneously between said electrodes (perfect homogeneity is not required, as long as the layer has the required conduction conditions—characterised for example by the resistivity of the layer in the case of an ohmic sensor or an antenna, or by the transconductance or the saturation current in the case of a transistor) and monitoring the quantity applied thereof, may be used, provided that the temperature constraints set by the nature of the support used are observed. Mention may particularly be made by way of deposition technique of dielectrophoresis or inkjet printing. These techniques result in carbon nanotubes regularly distributed between the electrodes. Further deposition techniques that may be envisaged are described in application WO 02/076724, particularly centrifugation deposition. Further details relating to the preparation of the carbon nanotubes and the deposition thereof may be found in applications US 2005/000830 and WO 2010/034840. It is also possible to deposit the electrodes on a previously formed carbon nanotube-based layer.

The composition comprising the carbon nanotubes is advantageously formulated by those skilled in the art so as to be able to carry out quality depositions on devices of which the size is of the order of a $cm^2$ to a fraction of a $mm^2$. Those skilled in the art are fully capable of optimising the deposition parameters, particularly in respect of printing, in order to achieve this result.

The chemical sensor has a layer of sensitive material according to the invention (generally a resistive material) having a thickness ranging, according to one embodiment, from 50 nm to 1 μm. This thickness is preferably less than 1 μm. The surface area of said layer of sensitive material is preferably less than 1 $cm^2$, preferentially less than 0.1 $cm^2$, more preferentially less than 1 $mm^2$.

The entirety of the device excluding a significant portion (at least 10%, preferably 100%) of the surface area) of the layer of functionalised carbon nanotubes may if required be coated with a passivation material, for example a resin such as PMMA. The support layer may also be passivated on the front and rear.

The composition according to the invention optionally contains additional compounds to increase the sensitivity of the sensor further, or conductive compounds, intended to enhance the performances of the electronic device forming the base of the sensor, or indeed surfactant compounds, to facilitate the deposition of the nanotubes.

In the case of a resistive sensor, the initial resistance of the sensor (before submerging in liquid), which is a key parameter of the final sensitivity of the sensor and of the integration thereof in a communicating system, may be finely monitored via the method and the specific deposition parameters of the carbon nanotubes. The layer of resistive material of the sensor according to the invention typically has a resistance ranging from $10^3$ ohms to $5.10^6$ ohms, preferably from $10^4$ ohms to $5.10^5$ ohms.

Finally, the sensor according to the present invention is associated, further, with means for applying an electric current or a given potential to the electrodes and monitoring at least one electrical feature of the sensor such as the resistance, conductance or impedance of the device. These means advantageously comprise one or a plurality of elements chosen from an electrical source such as a battery, means for connecting the electrodes to said electrical source such as a circuit, control means and measurement means so as to be able to set, track and/or monitor the potential applied to the electrodes and/or the resistance, conductance or impedance of the carbon nanotubes (and therefore the resistance of the device).

Figure 2:
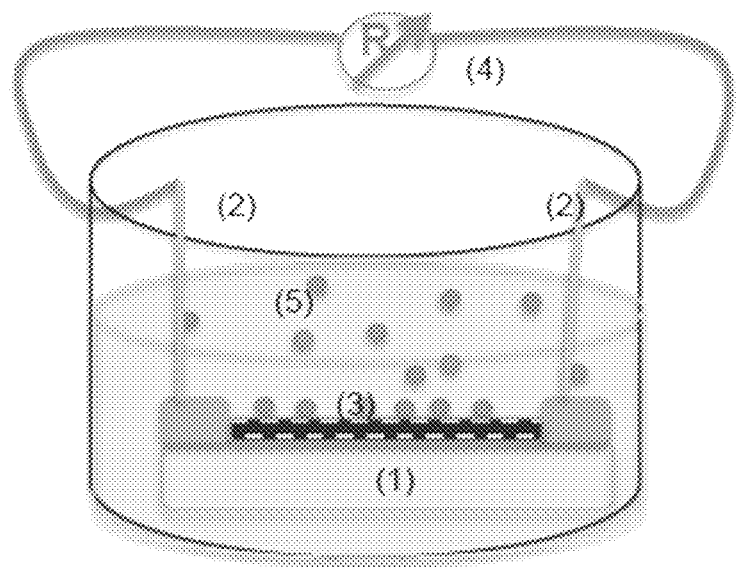
FIG. 2 is a schematic representation of an ohmic chemical sensor according to the present invention submerged in a solution under analysis.

FIG. 2 is a schematic representation of an ohmic chemical sensor according to the present invention, the size whereof has been exaggerated for visibility purposes. This device comprises a support (1), two conductive electrodes (2), a layer of sensitive material comprising functionalised carbon nanotubes (3) creating an electrical contact between the two electrodes and means (4) for tracking the variations of the resistance of the nanotubes due to exposure to analytes (5).

Figure 3:
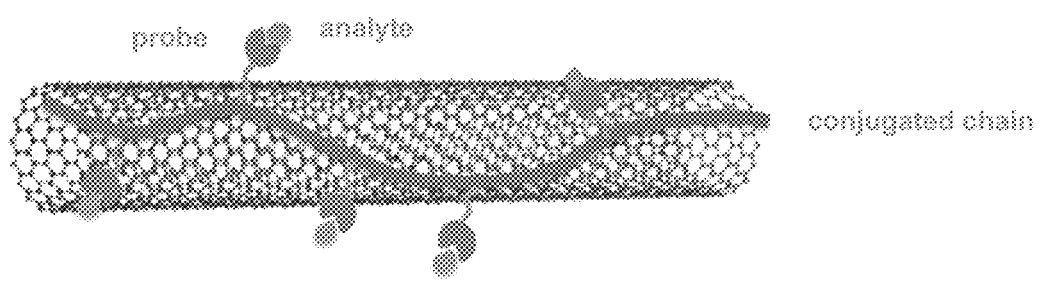
FIG. 3 is a schematic representation of a carbon nanotube functionalised by a conjugated polymer.

FIG. 3 is a schematic representation of a carbon nanotube functionalised by a conjugated polymer supporting side chains equipped with chemical probes intended for the detection of ionic analytes.

In practice, the sensor is submerged in the solution under analysis. Generally, the measurement method according to the invention comprises the measurement of the resistance (or of the relevant electrical parameter of the sensor in question) of the film of sensitive material thereof. The resistance of the device varies according to the concentration of the target analyte present in the solution, while having little or no sensitivity to the concentration of other analytes present in solution.

The variation of resistance is very rapid after the variation of concentration of the analyte. Indeed, the very good sensitivity of the sensors according to the invention stems from the very nature of the carbon nanotubes, which are electrical conductors known to give access to very sensitive devices to the environment thereof, and in that they are functionalised by conjugated polymers. The inventors think that chelation or reaction with an ionic compound induces a charge transfer which leads to the generation of carriers and to a modification of the electrical properties of the system.

Figure 4:
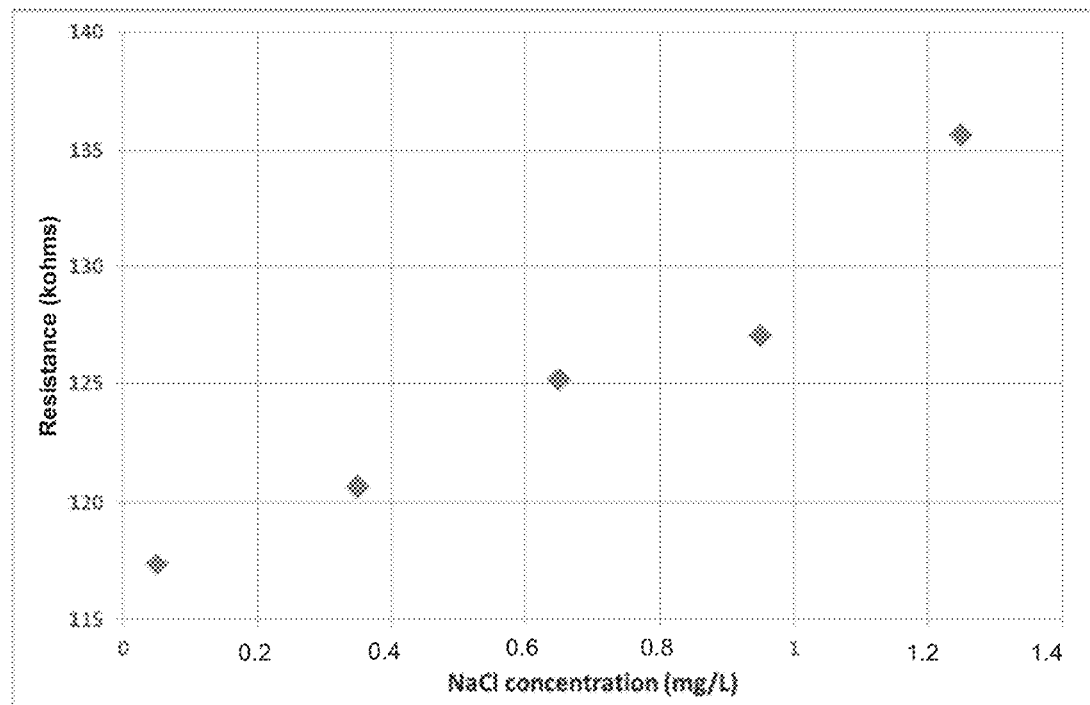
FIGS. 4 and 5 represent the variation of the resistance of two chemical sensors according to the invention according to, respectively, the NaCl and NaOCl concentration in an aqueous solution.
Figure 5:
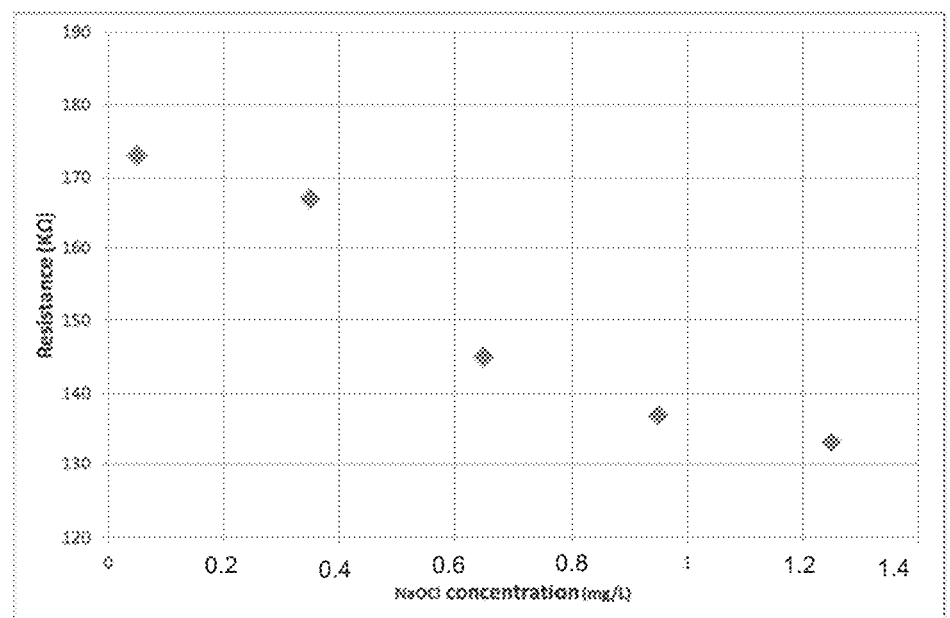

FIGS. 4 and 5 represent the variation of the resistance of two chemical sensors according to the invention according, respectively, to the concentration of NaCl and NaOCl in an aqueous solution (these sensors are respectively based on the conjugated polymers of examples 2 and 1 of the invention). Once such calibration curves have been obtained, an assay of the corresponding analytes, in this instance the chloride and hypochlorite ions, is possible in any aqueous solution. It was thus observed that the resistance of the chemical sensor was proportional, or depending on the case, inversely proportional, to the concentration of the target ionic species in solution.

The present invention therefore enables the chemical analysis of liquids such as water on-site and in real time, via a physical presence of an operator to read the measurements, or via real-time data reporting, for example by incorporating the chemical sensor into a communicating system with a view to wireless monitoring. The probe device comprising the sensor and the electronic system thereof may also function as a data recorder.

The invention enables indeed the production of selective, miniaturised, portable and inexpensive probes which enable the analysis of the chemical species by means of a simple measurement. These are generally reversible probes with a long service life, both idle and in continuous operation. They can withstand relatively high liquid flows without being degraded. It is also possible to design disposable probes.

The invention further enables the simultaneous analysis of various chemical species by means of a plurality of sensors incorporated in a single device (multiplexing), each sensor having a specific response to each species making up the system. The present invention therefore also relates to a system comprising one or a plurality of chemical sensors as defined above, identical or different, preferably at least two with a view to the detection and/or assay of at least two ionic chemical species in a fluid. Advantageously, such a system comprises at least 3 sensors, particularly at least 5 sensors, in particular at least 10 sensors, identical or different, such as those defined above. The use of a plurality of identical sensors makes it possible to verify the reproducibility of measurement, or compensate for any deficiency of a sensor. Of these sensors, some, even all, may be differentiated by the targeted analyte, i.e. by the nature of the conjugated polymer and in particular of the chemical probe thereof.

Figure 6:
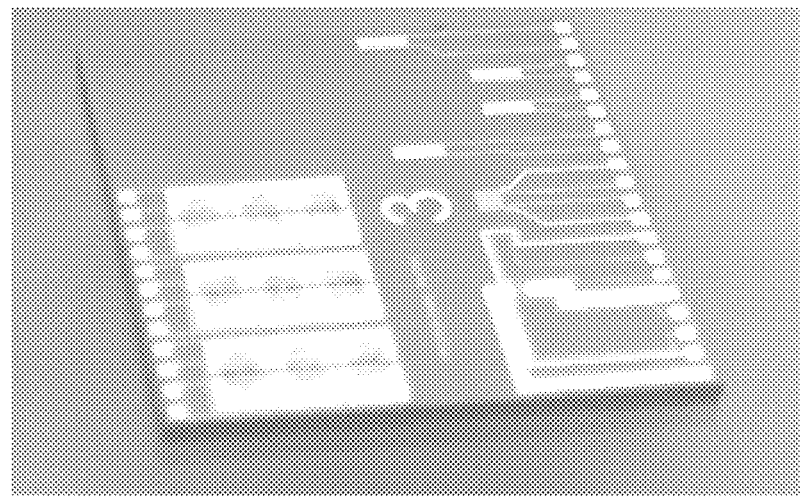
FIG. 6 is a photograph of a multifunction portable system including 9 chemical sensors according to the invention and FIG. 7 an image obtained by scanning electron microscopy of carbon nanotubes functionalised by the conjugated polymer of example 1 according to the invention.

FIG. 6 is a photograph of a multifunction portable system including 9 chemical sensors according to the invention.

The probe according to the present invention enables the detection at ambient temperature (18-25° C.) selectively and at low concentrations (<10 mg/L, preferably <0.05 mg/L) of ionic species, preferentially from inorganic chemical species, in particular the following analytes and mixtures thereof: hypochlorite ions, chloride ions, nitrate ions, phosphate ions, $Cu^+$, $Ag^+$, $Ca^{2+}$, $Mg^{2+}$, $Pb^{2+}$, $Hg^{2+}$, $Cd^{2+}$, $Cu^{2+}$, $Fe^{2+}$, $Ni^{2+}$, $Co^{2+}$, $Zn^{2+}$, $UO_2^{2+}$, $Fe^{3+}$, $Cr^{3+}$, $As^{3+}$ ions. In one embodiment, the analyte is a divalent or trivalent metallic cation, in particular a heavy metal cation. By heavy metal is understood in the present application ions from metals excluding alkaline and alkaline-earth metals.

The present invention also relates to the use of a chemical sensor or a system of chemical sensors as described above for the detection and/or assay of one or a plurality of ionic chemical species in a fluid, preferably in liquid medium, preferentially in an aqueous solution.

Similarly, the invention relates to a method for the detection and/or quantification of at least one ionic chemical species in a fluid, comprising a step consisting of placing a chemical sensor according to the invention in the environment wherein said species is present or likely to be present and of tracking the variation of at least one electrical characteristic of the chemical sensor, such as the resistance thereof, impedance thereof and/or conductance thereof.

Finally, the present invention relates to a method for the preparation of a chemical sensor intended to detect and/or assay at least one chemical compound as defined above, which comprises the deposition on a support, whereon are disposed at least two electrodes, of a layer of a composition comprising carbon nanotubes and a conjugated polymer according to the invention, such that said composition layer ensures electrical contact between the electrodes, particularly by dielectrophoresis or inkjet printing.

The carbon nanotubes may be deposited on top of the electrodes or the electrodes may be deposited partially on the nanotubes. Preferentially, the carbon nanotubes are deposited on top of the electrodes. The fact that the electrodes are at least partially coated with the composition layer of carbon nanotubes makes it possible to establish an electrical connection.

Preferably, the method for manufacturing the functionalised carbon nanotubes involves the functionalisation thereof after the dispersion thereof in a solvent and before the deposition thereof on a substrate.

In the case of grafting (covalent) of the conjugated polymer on the carbon nanotubes, the method comprises a step prior to deposition of grafting on the carbon nanotubes of the conjugated polymer and obtaining a dispersion of grafted nanotubes. This embodiment is more particularly described in application WO 2010/034840.

In the case of a non-covalent interaction, the method comprises a step prior to deposition of dispersion in a solvent of the carbon nanotubes and the conjugated polymer according to the invention.

The composition wherein are dispersed the carbon nanotubes and the conjugated polymer (optionally grafted) contains an organic solvent or alternatively an aqueous solvent, and may also contain a surfactant so as to stabilise the dispersion if the conjugated polymer does not allow such a stabilisation. This solvent is advantageously chosen in the group consisting of methanol, ethanol, propanol, isopropanol, ethyleneglycol, toluene, 1,2-dichlorobenzene, chlorobenzene, ethyl acetate, tetrahydrofuran, acetonitrile, acetone, dimethylformamide and dimethylsulphoxide. The solvent will be subsequently removed by any suitable technique. Advantageously, said surfactant belongs to a type chosen from anionic surfactants, cationic surfactants, zwitterionic surfactants and non-ionic surfactants and, in particular, the surfactants described in application WO 2009/083562. The carbon nanotubes are generally dispersed in the deposition composition using a mechanical stirring technique optionally combined with an ultrasound treatment. A combination of the two means usually supplies dispersions of greater quality. An additional centrifugation or sedimentation step may be envisaged to remove the agglomerates and obtain a uniform dispersion without large carbon nanotubes agglomerates.

The carbon nanotubes and/or the conjugated polymer are present in the composition in a quantity ranging typically from 0.1 to 10000 mg/L, preferably from 1 to 500 mg/L, preferentially from 10 and 400 mg/L and more preferentially from 50 and 300 mg/L, these quantities being dependent on the deposition method. The mass ratio of carbon nanotubes/conjugated polymer in the deposition composition varies generally from 0.4 to 2.5, preferentially from 0.5 to 2, and more preferentially from 0.8 to 1.2.

The chemical sensors according to the invention may be used in numerous fields, such as health, the environment, industry and defence, and are particularly useful for water analysis.

With respect to the chemical sensors enabling real-time measurement of analytes in water available on the market, the sensors according to the invention maximise the selectivity and sensitivity of the sensitive elements, with a factor 10 enhancement with respect to the commercial prior art. The total cost thereof, including the sensor per se and the electronics thereof is substantially lower and divides that of current systems by a factor of 10 to 100 depending on whether the sensor is produced in small or mass production runs. The size of the sensitive zone of the sensor is also very small, potentially attaining a fraction of a $mm^2$, versus a few $cm^2$ currently, or a division by more than a factor of 100. Finally, the sensors according to the invention are capable of supplying a measurement in some tens of seconds while current measurements usually require samples and an assaying action, followed by measurement by spectroscopy, extending over several hours (between the time of sampling on-site and the measurement in the laboratory).

The invention is illustrated, in a non-limiting manner, by the following examples.

EXAMPLES

Example 1: Synthesis of the Polymer of Formula 8 for the Detection and/or Quantification of Hypochlorite Ions The compound of formula 1 of the reaction diagram hereinafter is synthesised as described in *Photochemical and Photobiological Sciences*, 2013, 12, 284-297. The compound of formula 2 is synthesised as described in *Journal of Chemical Sciences*, 2015, 127, 383-394.

The compound of formula 7 is synthesised from compound 2 as follows. Compound 2 (850 mg; 0.15 mmol), 2,2'-(9,9-dihexyl-9H-fluorene-2,7-diyl)bis(1,3,2-dioxaborinane) (500 g; 0.85 mmol) and the catalyst Pd(PPh$_3$)$_4$ (50 mg; 0.04 mmol) are dissolved in 30 mL of degassed toluene. 6 mL of an aqueous potassium carbonate solution (590 mg; 4.27 mmol) is added. The reaction medium is heated to reflux in an inert atmosphere for 3 days. 9 µL (0.085 mmol) of bromobenzene is added to remove the terminal boronic arylester functions; after 6 hours of stirring, 10 mg (0.085 mmol) of phenylboronic acid is added to remove the terminal aryl bromide functions. The reaction medium is stirred for a further 6 hours, then cooled to ambient temperature (AT) and poured slowly into 400 mL of a methanol:water mixture (9:1). After filtration, the residue is washed with 100 mL of water and 100 mL of methanol, then dried. 550 mg of polymer of formula 7 (solid) is retrieved and washed by a Soxhlet with acetone.

$^1$H NMR: (300 MHz, CDCl$_3$): δ 10.20 (s, 1H), 8.55-8.31 (m, 2H), 8.21-8.00 (m, 2H), 7.90-7.24 (m, 16H), 2.00 (br, 4H), 1.10 (br, 12H), 0.65 (br, 10H). $^{13}$C NMR (75 MHz, CDCl$_3$, δ): 191.03, 151.85, 151.64, 143.37, 142.56, 142.48, 141.74, 140.45, 140.19, 140.00, 139.93, 139.82, 139.72, 135.69, 135.17, 134.74, 132.29, 132.14, 131.99, 131.59, 128.84, 128.69, 128.53, 127.23, 126.97, 126.69, 126.23, 124.79, 121.68, 121.60, 120.13, 120.01, 119.36, 119.11, 110.28, 55.46, 40.58, 31.53, 29.77, 23.88, 22.64, 14.11.

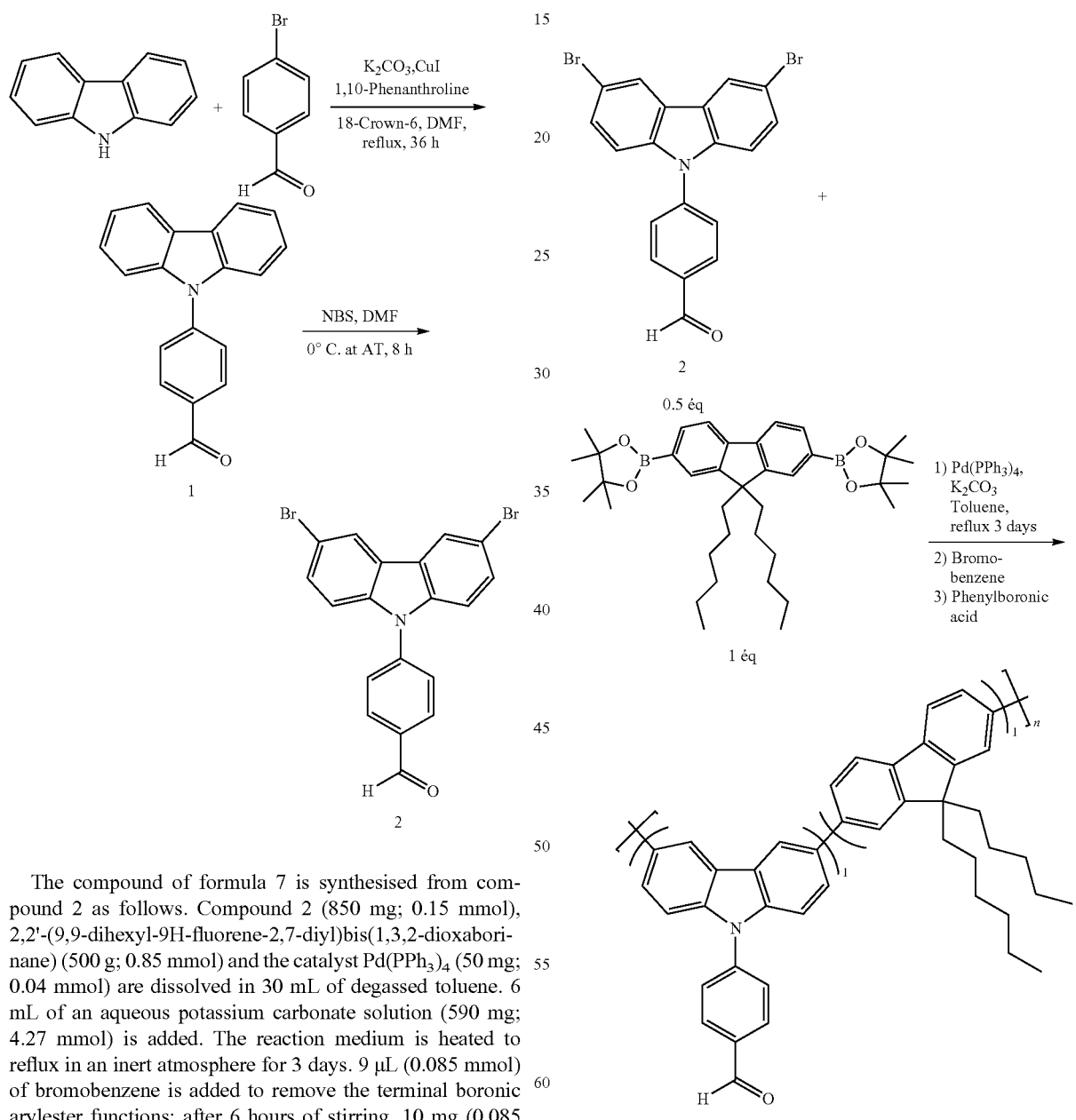

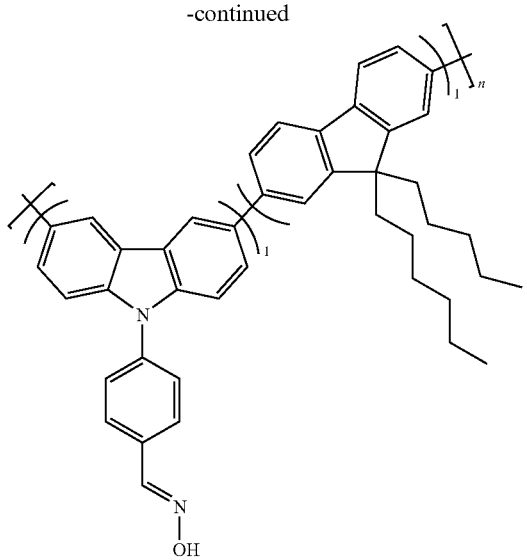

Compound 8

The polymer of formula 8 is synthesised as follows from the polymer of formula 7. 24 mg (0.34 mmol) of hydroxylamine hydrochloride is added to a solution containing 500 mg of compound 7 in 30 mL of a methanol:chloroform (1:1) mixture and 3 mL of triethylamine in an inert atmosphere. After 4 hours of stirring at 60° C., the solvent is evaporated, ethyl acetate is added to the solid residue, which is washed with a saturated sodium chloride solution, then with water. After drying, the solid obtained is purified by Soxhlet extraction with acetone. 500 mg of the polymer of formula 8 is obtained.

$^1$H NMR: (300 MHz, CDCl$_3$): δ 8.41 (br, 0.2H), 8.20 (br, 0.2H), 7.86-7.48 (m, 8H), 7.46-7.36 (m, 1H), 7.34-7.24 (m, 0.5H), 2.04 (br, 4H), 1.06 (br, 12H), 0.71 (br, 10H). $^{13}$C NMR: (75 MHz, CDCl$_3$): δ 151.82, 151.71, 141.74, 140.52, 140.42, 140.33, 140.11, 140.03, 139.99, 128.81, 128.60, 128.43, 127.22, 127.08, 126.15, 121.52, 120.00, 55.35, 40.40, 31.49, 29.71, 23.85, 22.59, 14.07.

Example 2: Synthesis of the Polymer of Formula 9 for the Detection and/or Quantification of Chloride Ions Compound 3 of the reaction diagram hereinafter is synthesised as described in *Macromolecules*, 2005, 38, 745-751: aniline is added to a mixture of 2,7-dibromo-9-fluorenone and aniline hydrochloride in an argon atmosphere. The reaction medium is heated to 150° C. for 6 hours, then cooled to ambient temperature. The reaction medium is poured into the water and extracted with ethyl acetate. Compound 3 is obtained after recrystallisation in hexane.

Compound 4 of the reaction diagram hereinafter was synthesised as follows. 0.22 mL (1.9 mmol) of phenyl isocyanate is added dropwise to a solution of 400 mg (0.8 mmol) of compound 3 in 10 mL of dichloromethane in an argon atmosphere. The reaction mixture is stirred for 4 hours at ambient temperature, then 20 mL of diethyl ether is added. Compound 4 (410 mg, 69% yield) is obtained in grey solid form after filtration and washing with 50 mL of diethyl ether and 20 mL of dichloromethane.

$^1$H NMR: (300 MHz, CDCl$_3$, 5): 8.43 (s, 2H), 8.35 (s, 2H), 7.71-7.54 (m, 2H), 7.45-7.24 (m, 12H), 7.22-7.09 (m, 4H), 7.02-6.93 (d, 4H), 6.92-6.83 (t, 2H). $^{13}$C NMR (75 MHz, CDCl$_3$, 5): 154.4, 154.1, 140.5, 139.7, 138.8, 138.7, 131.8, 129.9, 129.8, 129.2, 123.2, 123.0, 122.5, 119.8, 119.6, 65.5.

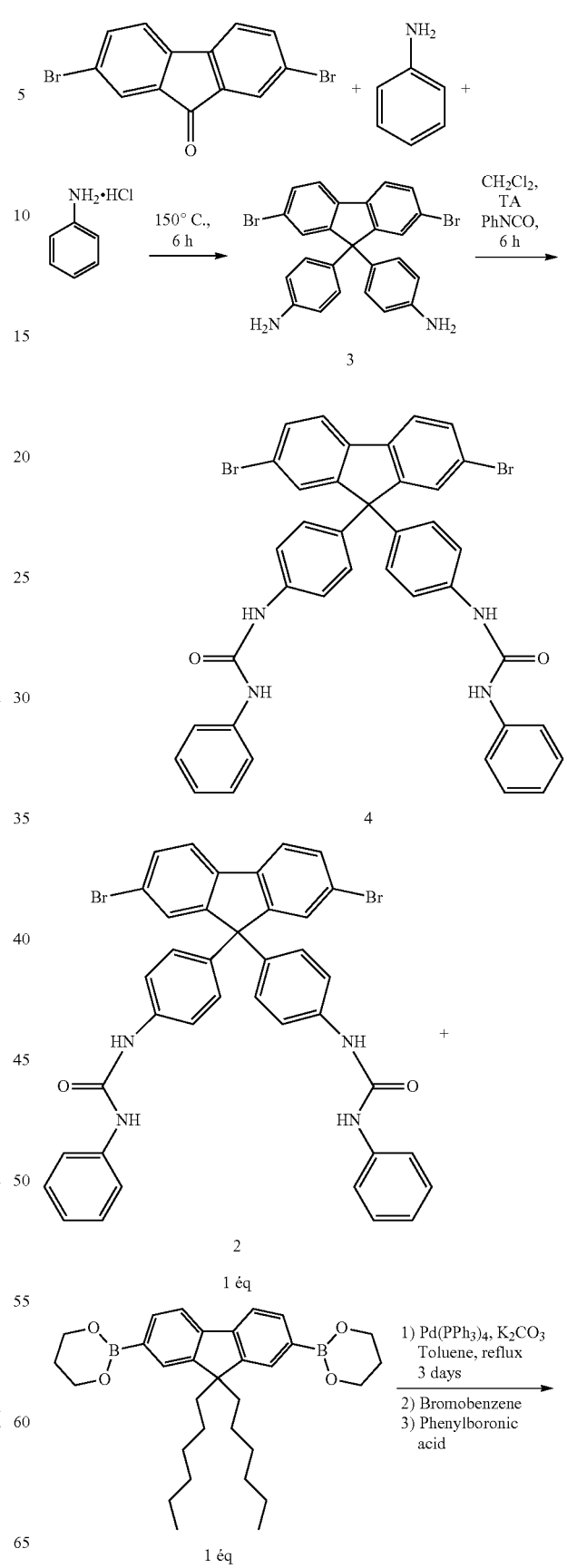

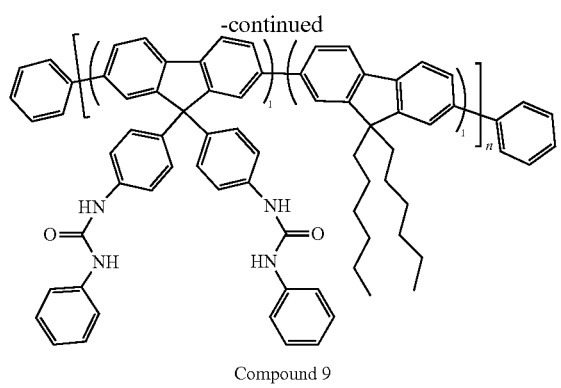

Compound 9

The polymer of formula 9 of the reaction diagram above, was synthesised as follows. (700 mg; 0.94 mmol) of compound 4, 2,2'-(9,9-dihexyl-9H-fluorene-2,7-diyl)bis(1,3,2-dioxaborinane) (530 mg; 0.94 mmol) catalyst Pd(PPh$_3$)$_4$ (50 mg; 0.005 mmol) are dissolved in 40 mL of a degassed 1,4-dioxane:toluene (1:1) mixture. 10 mL of an aqueous solution containing 650 mg (4.7 mmol) of potassium carbonate is added slowly. The reaction medium is heated to reflux in an inert atmosphere for 3 days, then 29 μL (0.28 mmol) of bromobenzene is added and, after 6 hours of stirring, 36 mg (0.28 mmol) of phenylboronic acid is added. After 6 hours of stirring at reflux, the reaction mixture is returned to ambient temperature and poured slowly into 200 mL of a methanol:water mixture (10:1), filtered and washed with water and methanol. The solid obtained is purified by Soxhlet extraction with acetone. 150 mg of the polymer of formula 9 are obtained.

$^1$H NMR (300 MHz, CDCl$_3$/DMSO): δ 8.35 (s, 2H), 8.00-6.78 (m, 26H), 6.64-6.40 (m, 2H), 2.0 (br, 2H), 1.0 (br, 23H), 0.6 (br, 10H). $^{13}$C NMR (75 MHz, CDCl$_3$/DMSO): δ 157.88, 156.51, 156.45, 156.43, 156.39, 150.92, 145.51, 144.67, 144.60, 144.44, 143.45, 143.18, 143.02, 138.93, 133.67, 133.65, 133.56, 133.34, 133.31, 133.12, 131.79, 131.33, 130.90, 129.15, 126.85, 125.86, 125.33, 124.92, 123.36, 123.17, 119.53, 119.50, 119.48, 69.30, 60.01, 36.35, 34.51, 33.78, 27.24, 18.91.

Example 3: Synthesis of the Polymer of Formula 10 for the Joint Detection and/or Quantification of Ca$^{2+}$ and Mg$^{2+}$ Ions Compound 5 of the reaction diagram hereinafter was synthesised from compound 3 of the reaction diagram hereinafter, as follows. 124 mg (0.9 mmol) of potassium carbonate and 15 mg (0.09 mmol) of potassium iodide are added to a solution containing 500 mg (1 mmol) of compound 3 in THF at ambient temperature. 1.38 g (9 mmol) of methyl bromoacetate is then slowly added. The reaction medium is stirred for 18 hours at 100° C., then poured into water. The precipitate is filtered and dried. 596 mg (0.75 mmol) of compound 5 is obtained in the form of a light orange solid.

$^1$H NMR (300 MHz, CDCl$_3$): δ 7.54-7.51 (d, 2H), 7.44-7.41 (d, 4H), 6.98-6.96 (d, 4H), 6.47-6.44 (t, 4H), 4.10 (s, 4H), 3.74 (s, 12H).

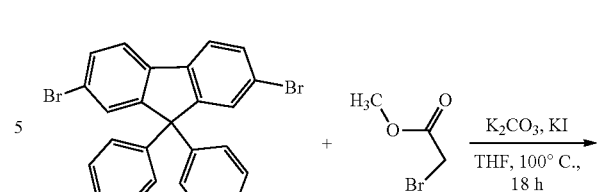

3
1 éq

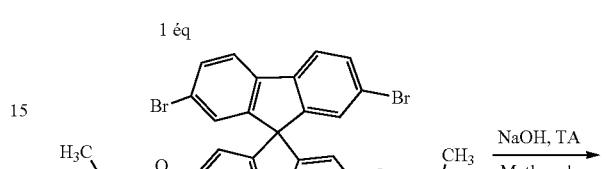

5
9 éq

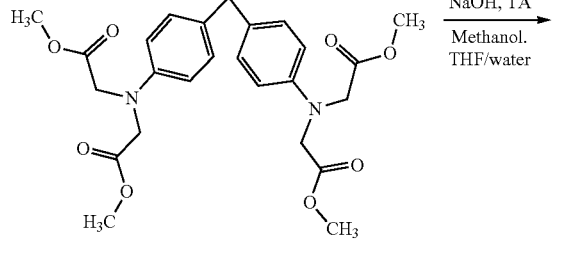

6

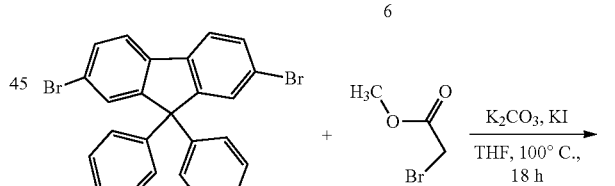

3

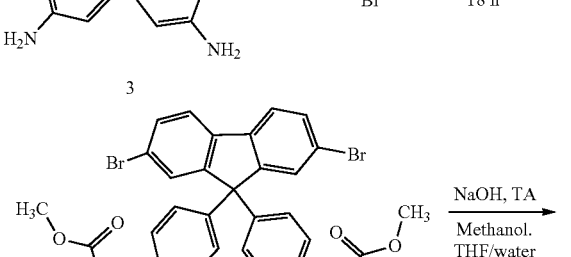

5

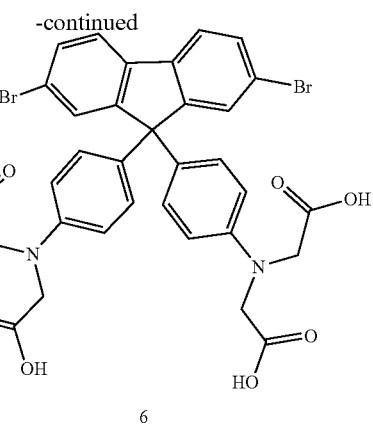

6

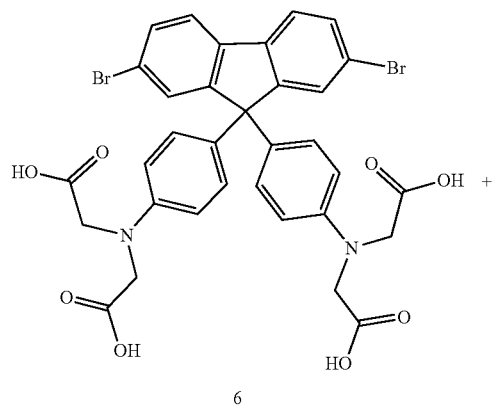

6

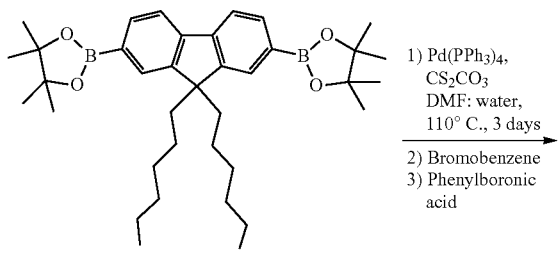

1) Pd(PPh₃)₄, CS₂CO₃ DMF: water, 110° C., 3 days
2) Bromobenzene
3) Phenylboronic acid

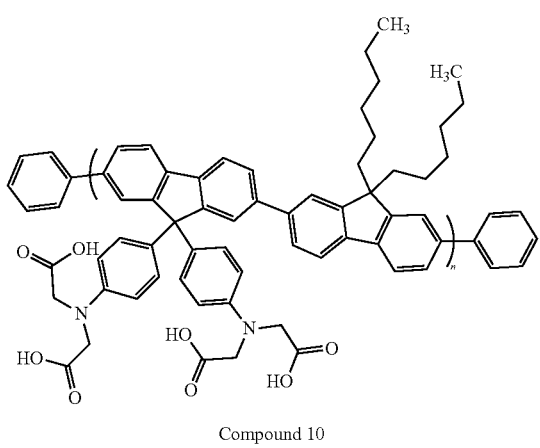

Compound 10

Compound 6 of the reaction diagram above was synthesised as follows. 2 ml (5 mmol) of an aqueous sodium hydroxide solution is added slowly to a solution of 477 mg of compound 5 (0.6 mmol) in methanol at 0° C. The reaction medium is stirred for 1 hour at ambient temperature, then the solvent is evaporated. The residue is taken up with water. Extraction with ethyl acetate after neutralising the aqueous solution provides 437 mg (0.57 mmol) of compound 6 in the form of a white solid.

$^1$H NMR (300 MHz, CDCl$_3$): δ 7.49-7.46 (d, 2H), 7.37-7.31 (m, 4H), 6.92-6.89 (d, 4H), 6.40-6.38 (d, 4H), 4.04 (s, 4H).

The polymer of formula 10 of the reaction diagram above was synthesised as follows. 107 mg (0.14 mmol) of compound 6, 70 mg (0.14 mmol) of 9,9-di-n-hexylfluorene 2,7-diboronic acid bipinacol ester and 130 mg (0.14 mmol) of caesium carbonate are dissolved in 5 mL of a dimethylformamide:water mixture (4:1). after degassing the reaction medium, 8 mg (0.007 mmol) of tetrakis(triphenylphosphine) palladium catalyst is added. The reaction medium is then stirred for 3 days at 110° C., then 5 µL (0.05 mmol) of bromobenzene is added and, after 6 hours of stirring, 6 mg (0.05 mmol) of phenylboronic acid is added. After 6 hours of stirring at reflux, the reaction mixture is returned to ambient temperature and poured slowly into 400 mL of ethanol, filtered and dried. The solid obtained is purified by Soxhlet extraction with acetone. 100 mg of polymer of formula 10 is obtained.

Example 4: Synthesis of the Polymer of Formula 12 for the Detection of Heavy Metal Ions The polymer of formula 12 of the reaction diagram hereinafter was synthesised rom compound 11, itself obtained according to the technique described in Polymer 48 (2007) 1245-1254. The synthesis of polymer 12 was performed as follows. 242 mg (0.41 mmol) of compound 11, 204 mg (0.41 mmol) of 9,9-dihexylfluorene-2,7-diboronic acid bis(1,3-propanediol), 24 mg (0.02 mmol) of tetrakis(triphenylphosphine)palladium(0) and 75 mg (1.28 mmol) of caesium carbonate are added to 5 mL of DMF in an inert atmosphere. The reaction medium is stirred at 110° C. for 72 hours. After cooling, 26 µl (0.16 mmol) of bromobenzene is added and after 5 hours of further stirring at 110° C., the reaction medium is cooled, then 19.5 mg (0.16 mmol) of phenylboronic acid is added. The mixture is stirred for 5 hours at 110° C., then cooled and poured dropwise into 200 mL of methanol. A grey precipitate is obtained. It is retrieved by filtration, dried and dissolved in a few mL of chloroform and poured once again into 200 mL of methanol. The whitish precipitate obtained is retrieved by filtration, dried, and purified by Soxhlet extraction with acetone for 2 days. 100 mg of polymer of formula 12 is obtained.

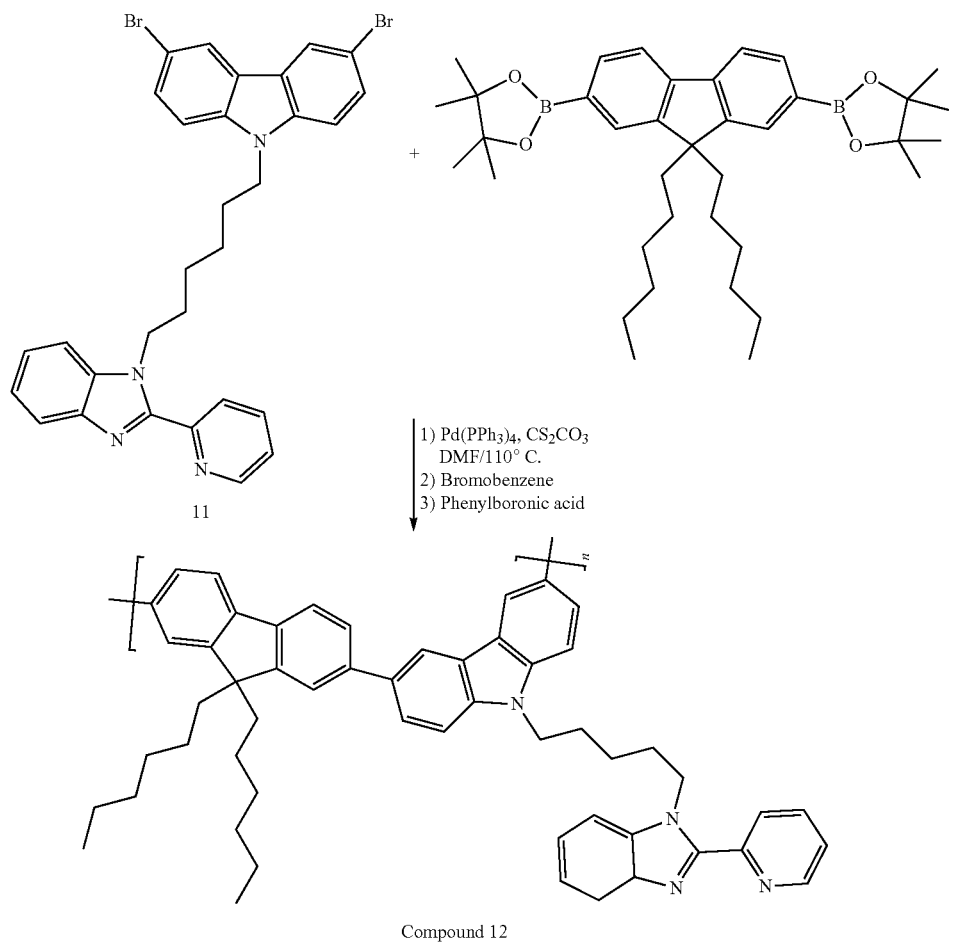

Compound 12

Example 5: Preparation of Carbon Nanotube Compositions Functionalised By Conjugated Polymers A composition which will serve as ink with a view to inkjet printing is prepared as follows. Firstly, a dispersion is prepared containing 0.02% by mass of carbon nanotubes in dichlorobenzene (200 mg/L), further comprising 0.03% by mass of the surfactant sodium dodecylbenzenesulphonate, by sonication and centrifugation. A solution of the conjugated polymer sought is then prepared in dichlorobenzene (1 mg/mL), and the suitable quantities of the carbon nanotube dispersion and the conjugated polymer solution are mixed to arrive at a composition comprising a mass ratio of carbon nanotubes/conjugated polymer of 1:1.

Figure 7:
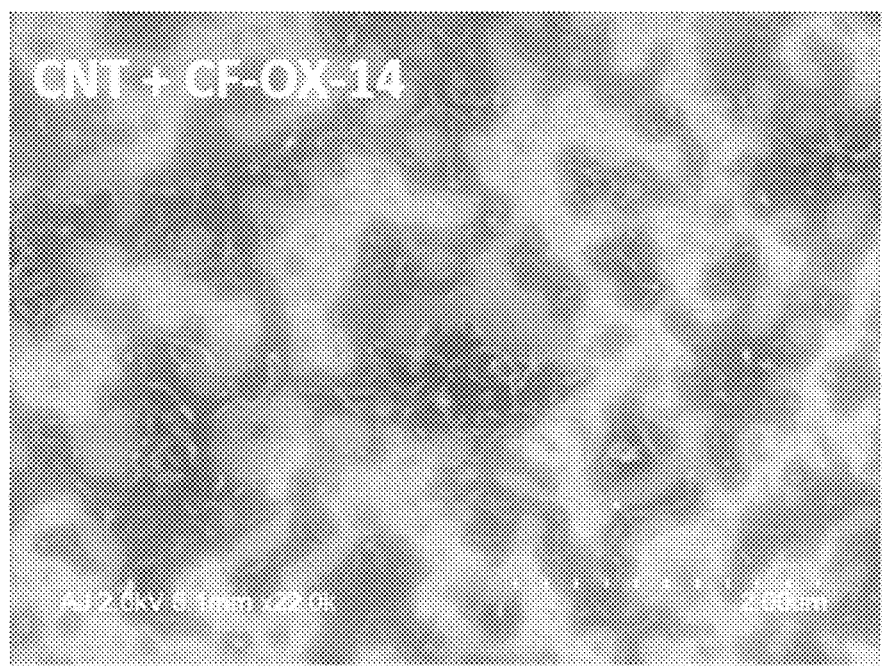

FIG. 7 shows an image obtained by scanning electron microscopy of carbon nanotubes functionalised by the conjugated polymer of example 1 according to the invention.

Example 6: Preparation of the Chemical Sensors

The compositions prepared in example 4 were deposited by means of an inkjet printer on a silica substrate between two electrodes, thus creating, after rinsing and drying, an electrical contact.

The process includes: 1) filling a cartridge with the suitable functionalised carbon nanotube composition; 2) cleaning the substrate with acetone and isopropanol; 3) printing 12 layers of functionalised carbon nanotubes on the substrate at ambient temperature according to a rectangular pattern; 4) drying at 150° C. on heating plate; 5) rinsing with acetone and with methanol for a few seconds. Repetition of steps 3 to 5 several times (up to 4) until the target resistance is attained (particularly resistance less than 500 KOhms).

The device composed of the electrodes and the resistive material is a sensor sensitive to hypochlorite ions (ClO$^-$) when the conjugated polymer is that of example 1, to chloride ions when the conjugated polymer is that of example 2, to $Ca^{2+}/Mg^{2+}$ ions when the conjugated polymer is that of example 3, to heavy metal ions when the conjugated polymer is that of example 4.

As shown in FIGS. 4 and 5, chemical sensors based on carbon nanotubes functionalised respectively by the conjugated polymers of examples 2 and 1 make it possible to assay, respectively, the chloride and hypochlorite ions present in an aqueous solution in concentrations ranging at least from 0.05 mg/L (50 ppb) to 1.25 mg/L (1.25 ppm).

The invention claimed is:

1. A conjugated polymer comprising monomer units A chosen from the monomer units of formulas:

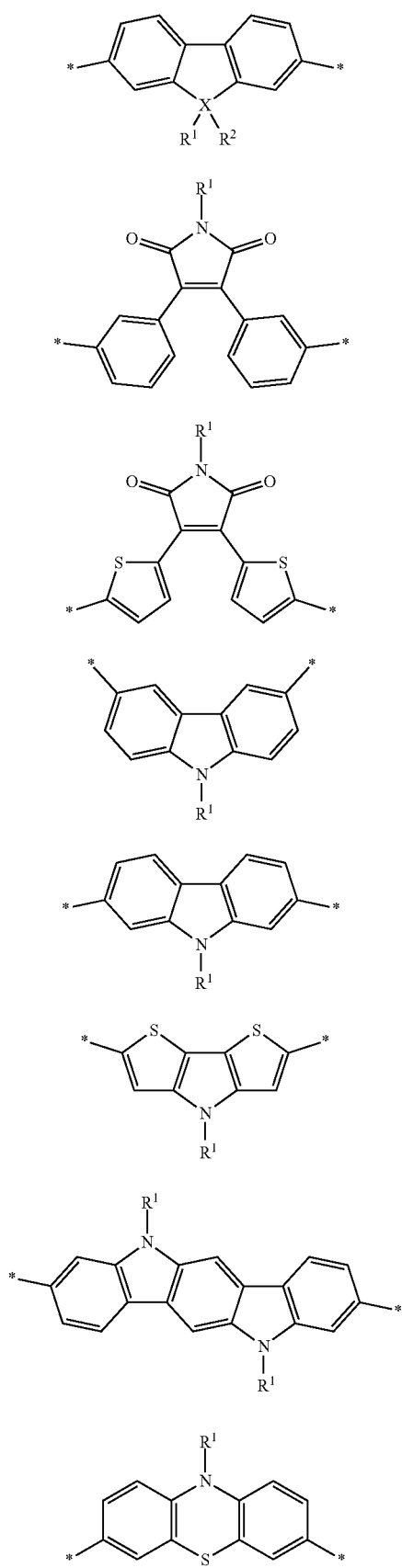

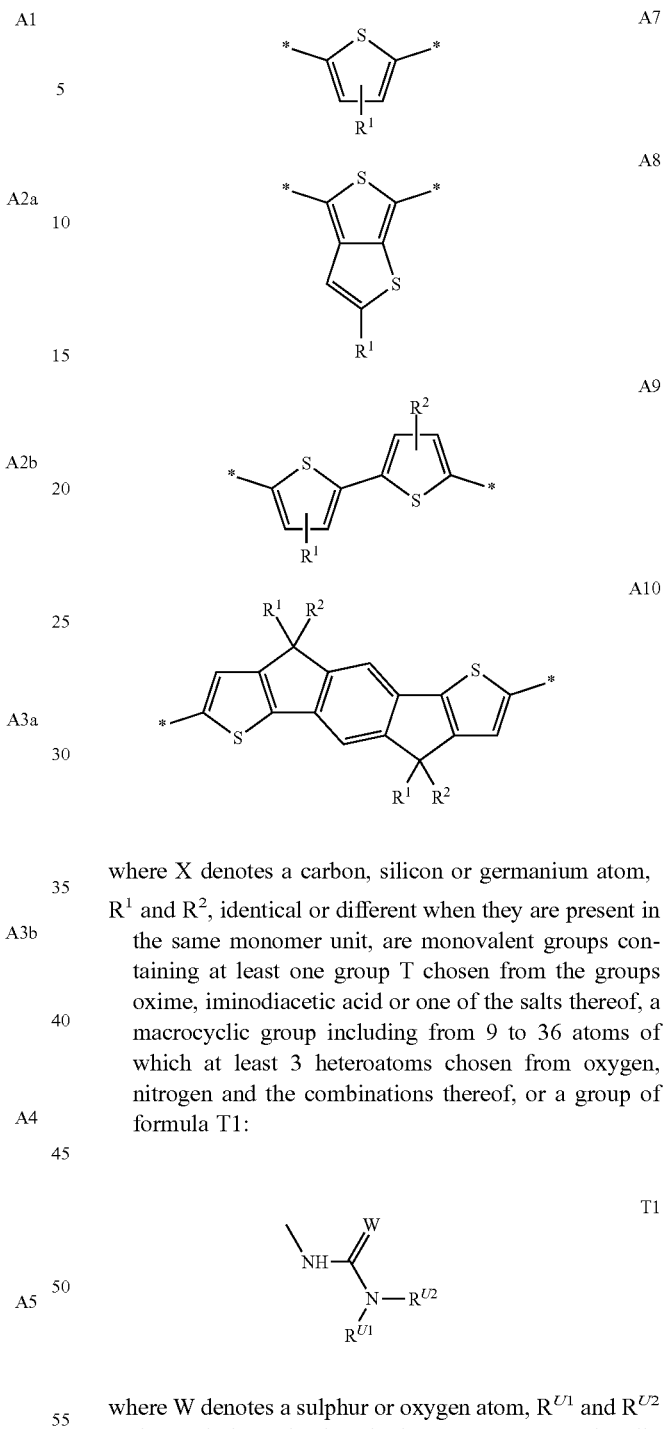

where X denotes a carbon, silicon or germanium atom,

R¹ and R², identical or different when they are present in the same monomer unit, are monovalent groups containing at least one group T chosen from the groups oxime, iminodiacetic acid or one of the salts thereof, a macrocyclic group including from 9 to 36 atoms of which at least 3 heteroatoms chosen from oxygen, nitrogen and the combinations thereof, or a group of formula T1:

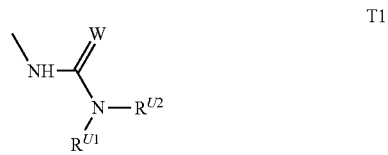

where W denotes a sulphur or oxygen atom, $R^{U1}$ and $R^{U2}$ denote independently a hydrogen atom, an optionally substituted alkyl group or an aryl group, ——— denotes the attachment point of the monomer unit to the polymer chain, the carbon atoms of the monomer units A being optionally substituted, and the groups R1 and/or R2 are groups of formula -L-T, where L denotes a divalent group.

2. The conjugated polymer of claim 1, further comprising monomer units B chosen from the monomer units of formulas:

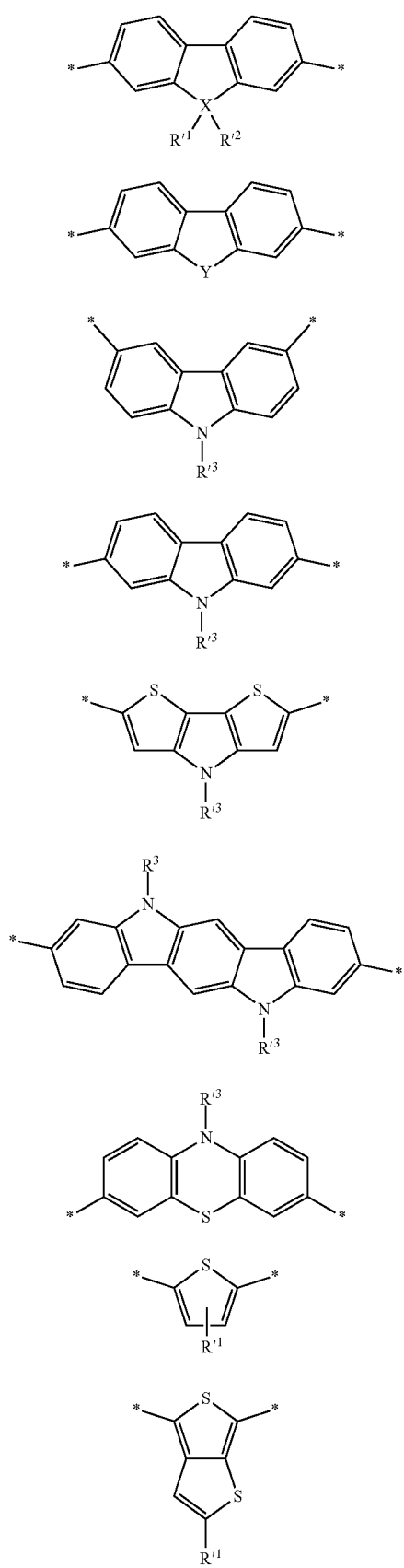
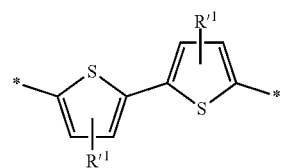
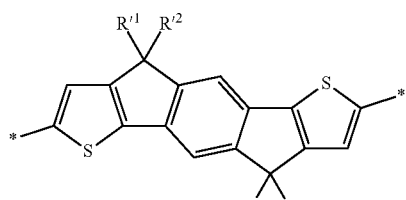
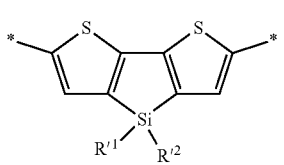
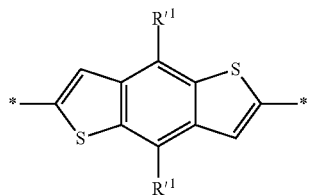
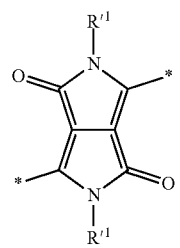
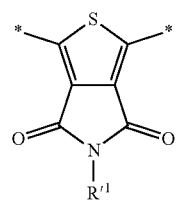
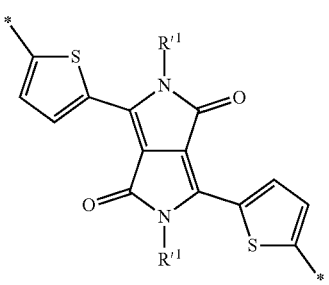
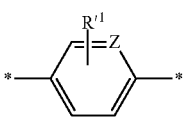

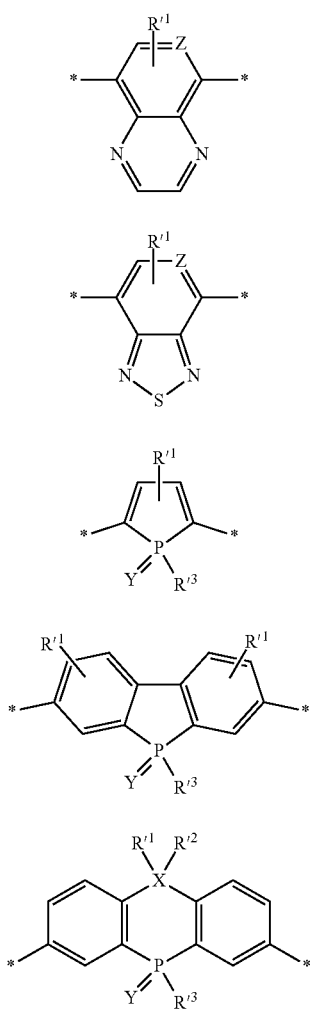

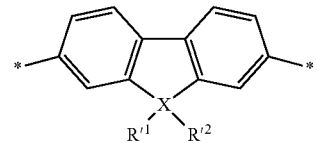

where X denotes a carbon, silicon or germanium atom;
— denotes the attachment point of the monomer unit to the polymer chain, and
the groups $R'^1$ and $R'^2$, identical or different when they are present in the same monomer unit, represent alkyl or alkoxyl groups comprising from 4 to 20 carbon atoms, linear or branched.

4. The conjugated polymer of claim 1, wherein it comprises monomer units of formula A3a or A3b, where L denotes a divalent group and T comprises at least one oxime function:

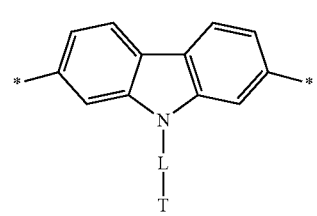

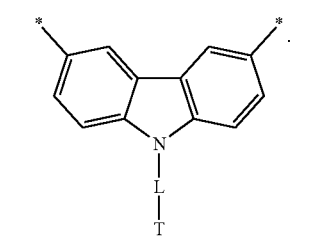

where X denotes a carbon, silicon or germanium atom; Y denotes a sulphur, oxygen or selenium atom; Z denotes a carbon or nitrogen atom, the carbon atoms of the monomer units B being optionally substituted, — denotes the attachment point of the monomer unit to the polymer chain, the groups $R'^1$ and $R'^2$, identical or different when they are present in the same monomer unit, represent alkyl or alkoxyl groups comprising from 4 to 20 carbon atoms, linear or branched, the group $R'^3$ represents an alkyl group comprising from 4 to 20 carbon atoms, linear or branched, an aryl group substituted by one or a plurality of alkyl groups comprising from 4 to 20 carbon atoms, linear or branched, or an acyl group of formula —C(O)$R'^5$, where $R'^5$ represents an alkyl group comprising from 4 to 20 carbon atoms, linear or branched, the group $R'^4$ represents an aryl group or an alkyl group comprising from 4 to 20 carbon atoms, linear or branched.

3. The conjugated polymer of claim 1, further comprising monomer units of formula B1a:

5. The conjugated polymer of claim 1, wherein it comprises monomer units of formulas A1a' or A1a", where L denotes a divalent group, T1 is as defined in claim 1 and T2 includes an iminodiacetic acid group or one of the salts thereof connected via the nitrogen atom thereof:

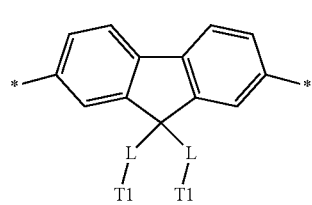

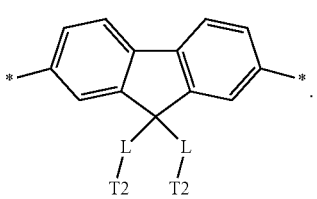

6. The conjugated polymer of claim 1, wherein it complies with one of the following formulas:

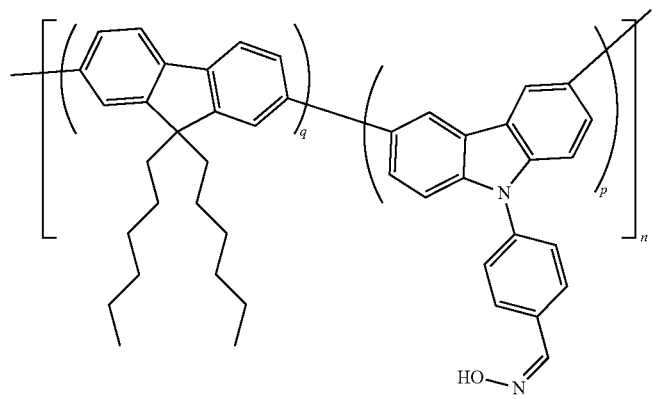
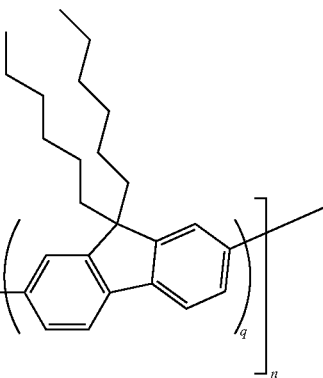
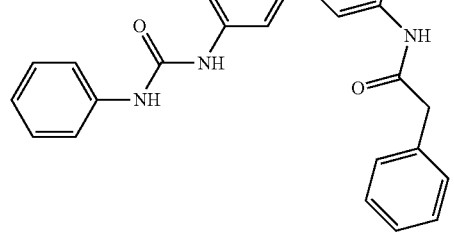
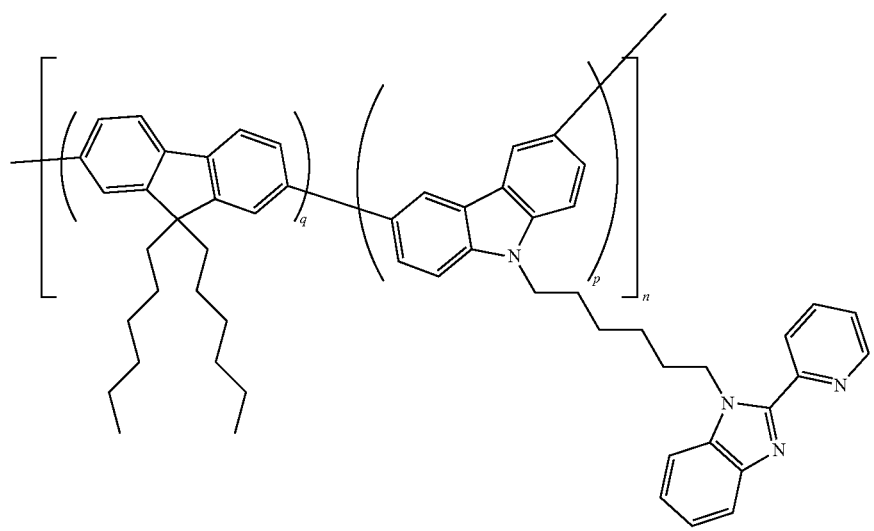

-continued
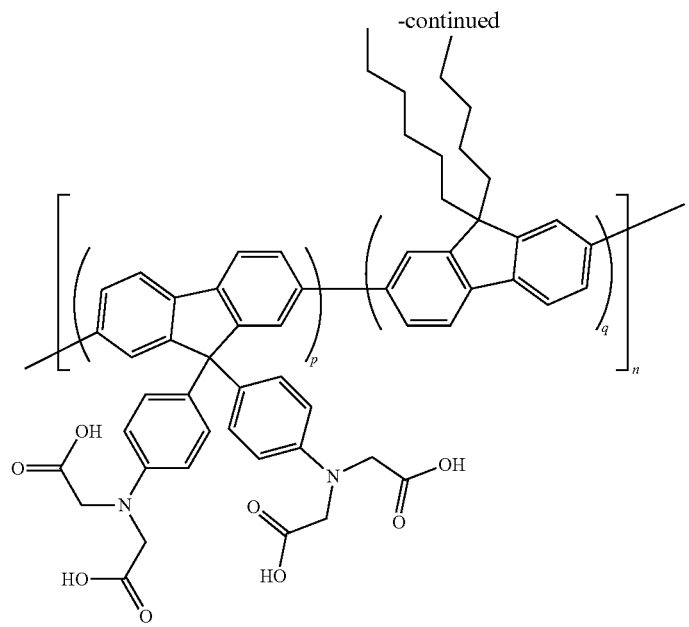
wherein p and q are identical or different integers ranging from 1 to 5 for p and from 0 to 20 for q and n denotes the degree of polymerisation.
7. A carbon nanotubes functionalised by at least one conjugated polymer comprising monomer units A chosen from the monomer units of formulas:
A1
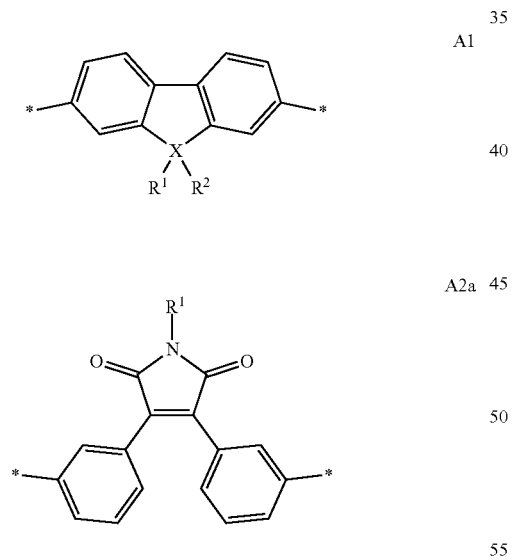
A2a
A2b
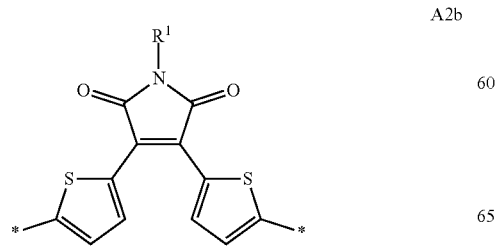
-continued
A3a
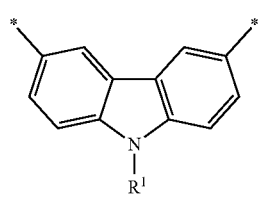
A3b
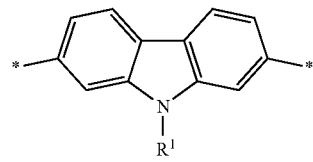
A4
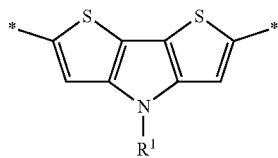
A5
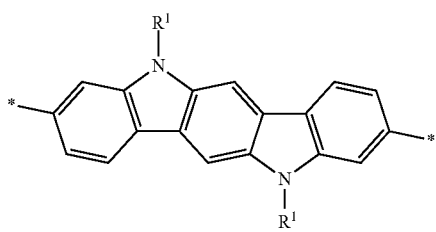

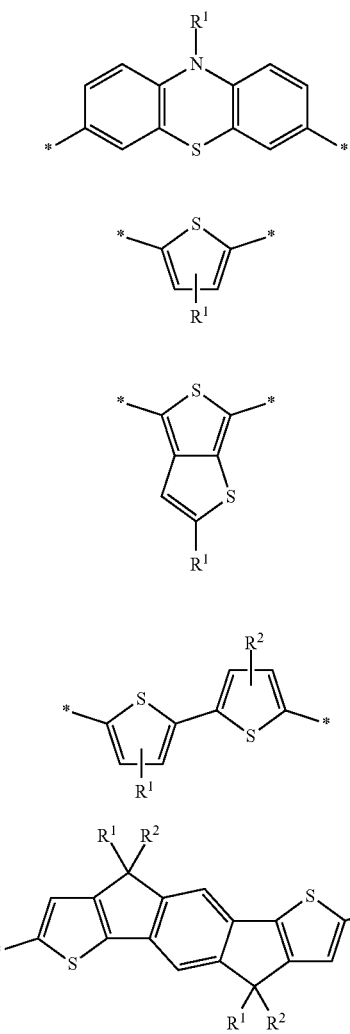

where X denotes a carbon, silicon or germanium atom, $R^1$ and $R^2$, identical or different when they are present in the same monomer unit, are monovalent groups containing at least one group T chosen from the groups oxime, iminodiacetic acid or one of the salts thereof, a polydentate Lewis base including at least two coordinating nitrogen and/or oxygen atoms, a macrocyclic group including from 9 to 36 atoms of which at least 3 heteroatoms chosen from oxygen, nitrogen and the combinations thereof, or a group of formula T1:

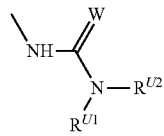

where W denotes a sulphur or oxygen atom, $R^{U1}$ and $R^{U2}$ denote independently a hydrogen atom, an optionally substituted alkyl group or an aryl group, —·— denotes the attachment point of the monomer unit to the polymer chain, the carbon atoms of the monomer units A being optionally substituted, and the groups $R^1$ and/or $R^2$ are groups of formula -L-T, where L denotes a divalent group.

8. The carbon nanotubes of claim 7, wherein the functionalisation of the carbon nanotubes by said at least one conjugated polymer is of non-covalent nature.

9. The carbon nanotubes of claim 7, wherein the conjugated polymer complies with one of the following formulas:

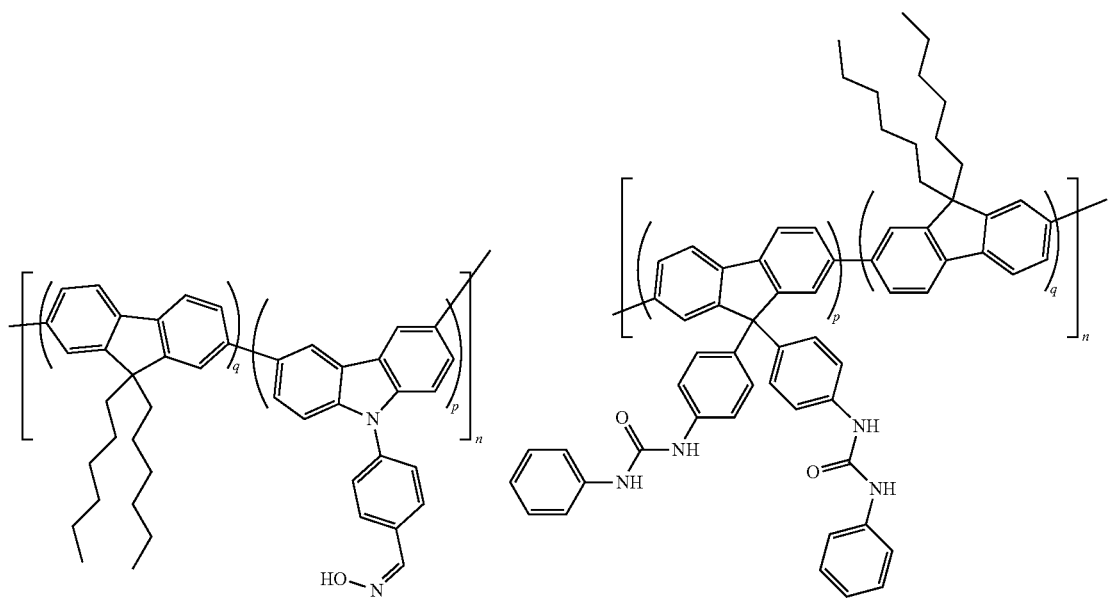

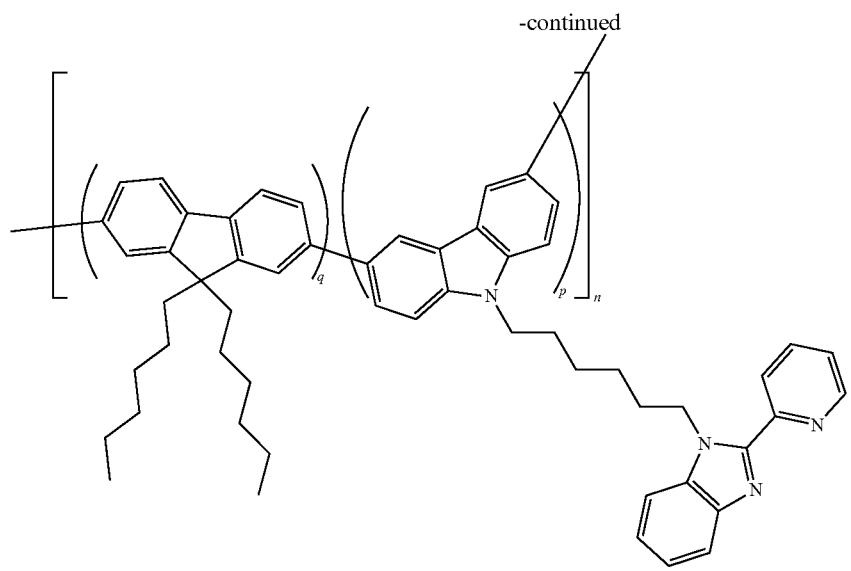

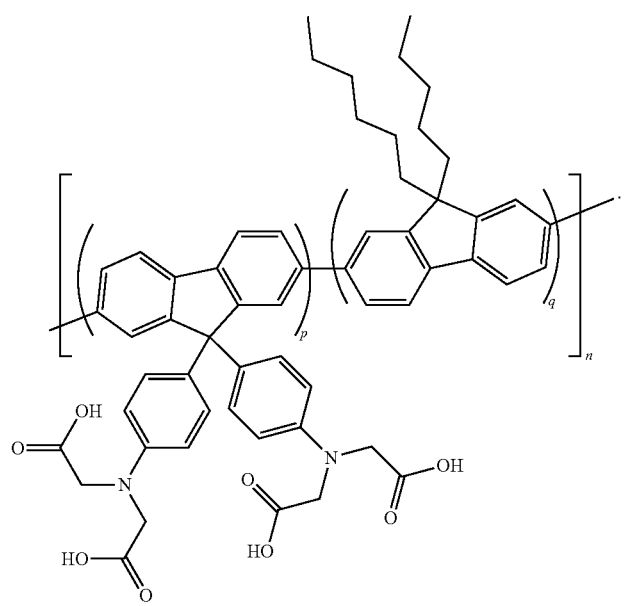

10. The carbon nanotubes of claim 7, wherein the group T is a polydentate Lewis base including at least two coordinating nitrogen atoms chosen from the following groups, optionally substituted: 2,2'-bipyridine (D5), 1,10-phenanthroline (D4), 2,9-dimethyl-1,10-phenanthroline, 1,10-phenanthroline-5,6-dione, imidazo[4,5-f]-1,10-phenanthroline of formula D1, 2,2'-bipyrimidine (D3), 2,2': 6',2"-terpyridine (D7), dipyrido-[3,2-a:2,3'-c]phenazine (D2), a 2,6-bis(2-benzimidazolyl)pyridine of formula D6, a 2-(2-pyridyl)benzimidazole of formula D8, thiabendazole (D9), $R^3$, $R^{3a}$ in the formulas hereinafter denoting independently from one another a hydrogen atom or an optionally substituted alkyl, optionally substituted alkylene, aryl, or arylene group:

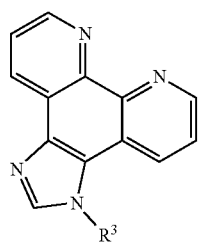

D1

-continued

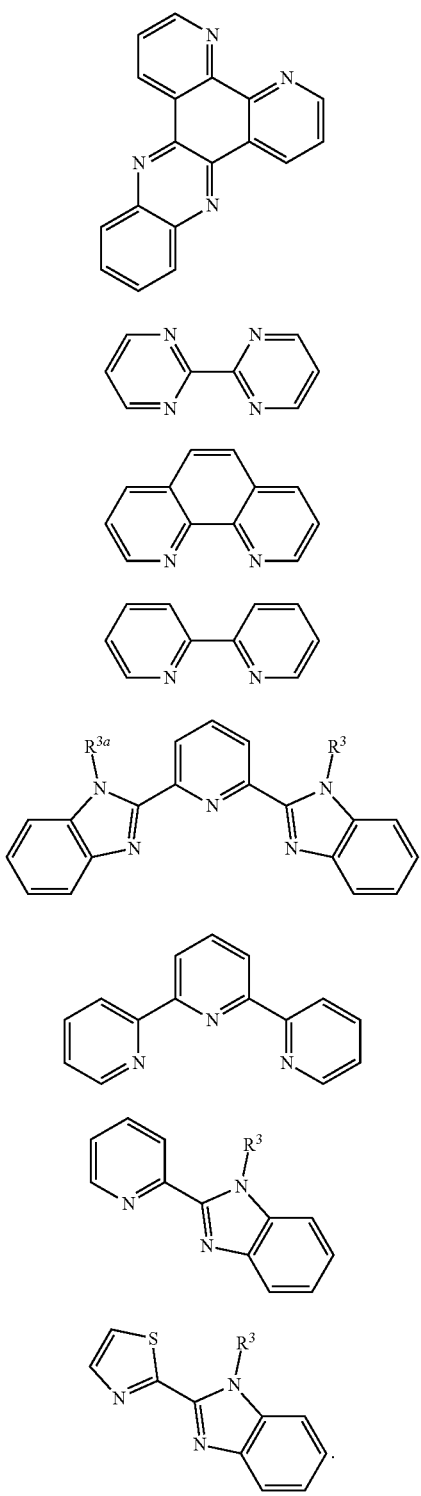

11. A system for the detection and/or assay of one or a plurality of ionic chemical species in a fluid, comprising at least one chemical sensor, said chemical sensor comprising a support and at least two electrodes disposed on said support, the support being at least partially coated with a layer of a composition comprising carbon nanotubes functionalised by at least one conjugated polymer of claim 1, said composition layer ensuring electrical contact between the electrodes and forming the sensitive element of the sensor.

12. The system of claim 11, comprising at least two chemical sensors, for the detection and/or assay of at least two ionic chemical species in a fluid.

13. The system of claim 11, wherein the ionic chemical species is chosen from hypochlorite, chloride, nitrate, phosphate ions, $Cu^+$, $Ag^+$, $Ca^{2+}$, $Mg^{2+}$, $Pb^{2+}$, $Hg^{2+}$, $Cd^{2+}$, $Cu^{2+}$, $Fe^{2+}$, $Ni^{2+}$, $Co^{2+}$, $Zn^{2+}$, $UO_2^{2+}$, $Fe^{3+}$, $Cr^{3+}$ and $As^{3+}$ ions.

14. A method for manufacturing a system, for the detection and/or assay of one or a plurality of ionic chemical species in a fluid, comprising at least one chemical sensor, said chemical sensor comprising a support and at least two electrodes disposed on said support, the support being at least partially coated with a layer of a composition comprising carbon nanotubes functionalised by at least one conjugated polymer of claim 1, said composition layer ensuring electrical contact between the electrodes and forming the sensitive element of the sensor, the method comprising:
  deposition on a support, whereon are disposed at least two electrodes, of a layer of a composition comprising carbon nanotubes and the at least one conjugated polymer, such that said composition layer ensures electrical contact between the electrodes.

15. The method of claim 14, wherein said deposition is carried out by inkjet printing.

16. The detection and/or assay method, comprising:
  providing a system of claim 11,
  using the system for the detection and/or assay of one or a plurality of ionic chemical species in a fluid.

17. The method of claim 16, wherein the fluid is an aqueous solution.

18. The conjugated polymer of claim 1, comprising monomer units A chosen from the monomer units of formulas:

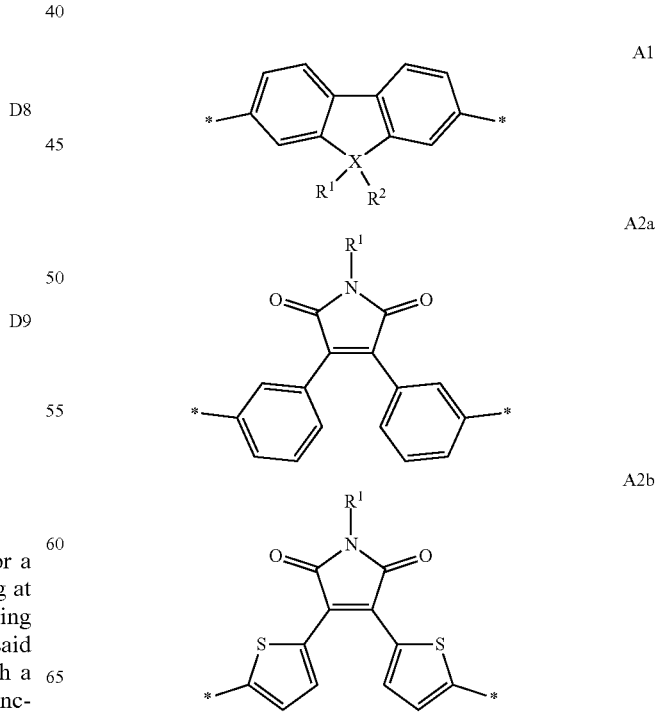

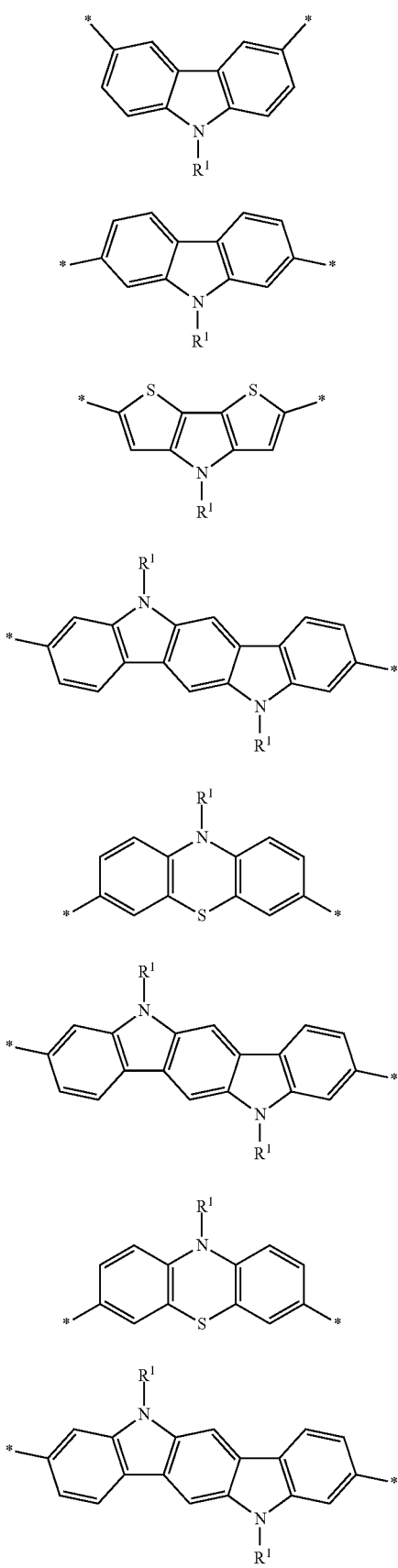
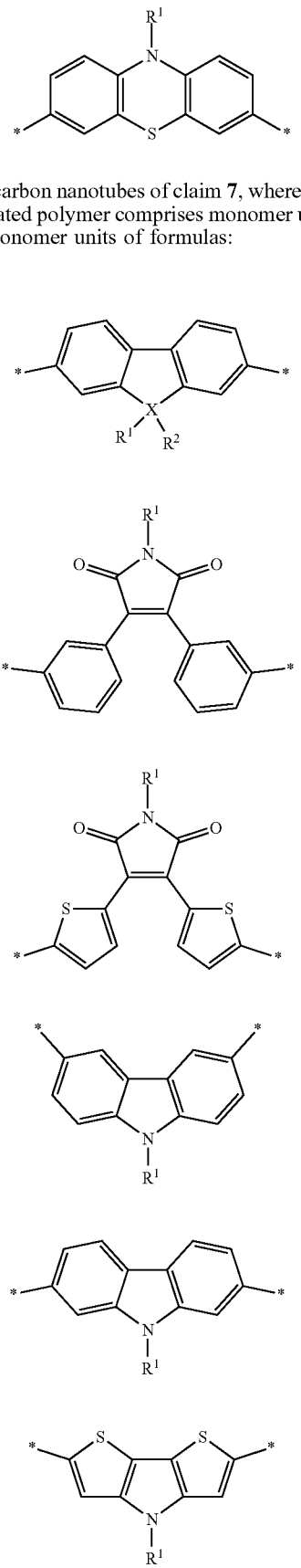
19. The carbon nanotubes of claim 7, wherein said at least one conjugated polymer comprises monomer units A chosen from the monomer units of formulas:

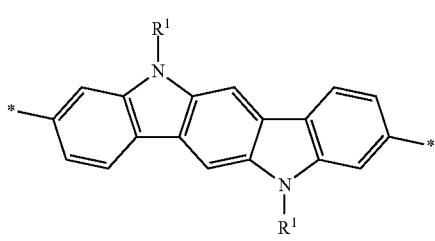 A5
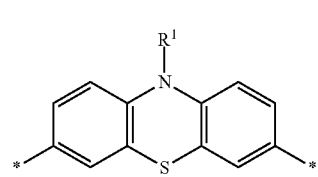 A6
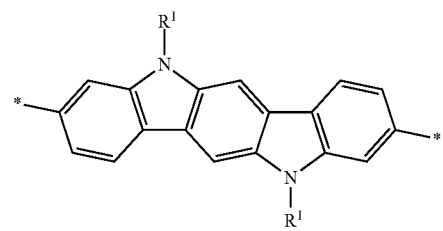 A5
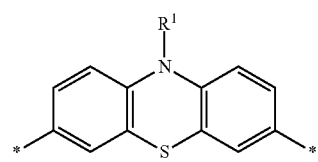 A6
* * * * *